(12) United States Patent
Suzuki

(10) Patent No.: US 8,106,002 B2
(45) Date of Patent: Jan. 31, 2012

(54) ANTI-CANCER AGENT COMPRISING PROTEIN C INHIBITOR

(75) Inventor: Koji Suzuki, Mie (JP)

(73) Assignees: Chugai Seiyaku Kabushiki Kaisha, Tokyo (JP); Mie University, Mie (JP)

( * ) Notice: Subject to any disclaimer, the term of this patent is extended or adjusted under 35 U.S.C. 154(b) by 414 days.

(21) Appl. No.: 11/911,754

(22) PCT Filed: Apr. 18, 2006

(86) PCT No.: PCT/JP2006/308095
§ 371 (c)(1),
(2), (4) Date: May 30, 2008

(87) PCT Pub. No.: WO2006/112451
PCT Pub. Date: Oct. 26, 2006

(65) Prior Publication Data
US 2009/0170760 A1    Jul. 2, 2009

(30) Foreign Application Priority Data

Apr. 18, 2005    (JP) ................... 2005-120083

(51) Int. Cl.
| A61K 38/00 | (2006.01) |
| A61K 35/00 | (2006.01) |
| A61K 38/55 | (2006.01) |
| A61K 38/16 | (2006.01) |
| C07K 14/00 | (2006.01) |

(52) U.S. Cl. ...... 514/1.1; 514/19.2; 514/19.3; 514/19.4; 514/20.1; 514/20.3; 530/350; 530/380

(58) Field of Classification Search .................. None
See application file for complete search history.

(56) References Cited

U.S. PATENT DOCUMENTS

| 6,593,291 | B1 * | 7/2003 | Green et al. .............. 514/2 |
| 2003/0105000 | A1 * | 6/2003 | Pero et al. ............... 514/12 |
| 2009/0035320 | A1 | 2/2009 | Suzuki et al. |

FOREIGN PATENT DOCUMENTS

| EP | 0 280 135 | 8/1988 |
| JP | 63-233927 | 9/1988 |
| JP | 2002-000273 | 1/2002 |
| WO | WO 01/62281 | 8/2001 |
| WO | WO 03/080646 | 10/2003 |
| WO | WO 03/083104 | 10/2003 |
| WO | WO 2004/065418 | 8/2004 |

OTHER PUBLICATIONS

Asanuma et al., Int. J. Cancer (2007) vol. 121, pp. 955-965.*
Bowie et al. (Science, 1990, 247:1306-1310).*
Skolnick et al. (TIBTECH 18:34-39, 2000).*
Ibragimova and Eade (Biophysical Journal, Oct. 1999, vol. 77, pp. 2191-2198).*
Burgess et al. (J of Cell Bio. 111:2129-2138, 1990).*
Scott et al. (Nature Genetics, 1999, 21:440-443).*
Miao et al. (Blood 2002: 100:3245-3252).*
Luo et al. (Biol. Chem.2006 387:813-816).*
Akita et al., "Protein C Inhibitor (PCI) inhibits invasion and matastasis of melanoma cells", Japanese Journal of Thrombosis and Hemostasis, 14(5):443, 2003.
Elisen et al., "Protein C Inhibitor Acts As A Procoagulant by Inhibiting the Thrombomodulin-Induced Activation of Protein C in Human Plasma", Blood, 91:1542-1547, 1998.
Francis Jr. et al., "Behaviour of Protein C Inhibitor in Intravascular Coagulation and Liver Disease", Thromb Haemostas, 52:71-74, 1984.
Hayashi et al., "Characterization of a Novel Human Protein C Inhibitor (PCI) Gene Transgenic Mouse Useful for Studying the Role of PCI in Physiological and Pathological Conditions", Journal of Thrombosis and Haemostas, 2:949-961, 2004.
Jackson et al., "Assessment of the interaction between urokinase and reactive site mutants of protein C inhibitor", Journal of Protein Chemistry 16(8):819-828, 1997.
Joyce et al., "Gene Expression Profile of Antithrombotic Protein C Defines New Mechanisms Modulating Inflammation and Apoptosis", The Journal of Biological Chemistry, 276:11199-11203, 2001.
Kaido et al., "Expressions of Molecules Associated with Hepatocyte Growth Factor Activation After Hepatectomy in Liver Cirrhosis", Hepato-gastroenterology, 51:547-551, 2004.
Marlar et al., "Deficiency of Protein C Inhibitor in Combined factor V/VIII Deficiency Disease", J. Clin. Invest., 66:1186-1189, 1980.
Suzuki et al., "Mechanism of Inhibition of Activated Protein C", J. Biochem. 95:187-195, 1984.
Suzuki et al., "Protein C Inhibitor Plays a Role as a Potent Regulator of Activated Hepatocyte Growth Factor Activator", Journal of Thrombosis and Haemostasis, 3(Suppl. 1):Abstract No. OR001, Abstracts from XXth ISTH Congress, Aug. 2005.
Suzuki, "Protein C Inhibitor (PAI-3): Structure and Multi-Function", Fibrinolysis and Proteolysis, 14:133-145, 2000.
Taylor Jr. et al., "DEGR-Factor Xa Blocks Disseminated Intravascular Coagulation Initiated by *Escherichia coli* Without Preventing Shock or Organ Damage", Blood, 78:364-368, 1991. Taylor Jr. et al., "Protein C Prevents the Coagulopathic and Lethal Effects of *Escherichia coli* Infusion in the Baboon", J. Clin. Invest., 79:918-925, 1987.
Wakita et al., "Regulation of carcinoma cell invasion by protein C inhibitor whose expression is decreased in renal cell carcinoma", Intl. J. Cancer 108(10):516-523, 2004.
Xue et al., "Hepatocyte Growth Factor Gene Therapy Accelerates Regeneration in Cirrhotic Mouse Livers After Hepatectomy", Gut, 52:694-700, 2003.
Kuhn et al., "Elicidating the structural chemistry of glycosaminoglycan recognition by protein C inhibitor", Proc. Natl. Acad. Sci. USA 87:8506-8510, 1990.
Shirk et al., "Role of the H helix in heparin binding to protein C inhibitor", The Journal of Biological Chemistry 269(46):28690-28695, 1994.
Stief et al., "Evidence for identity of PCI and plasminogen activator inhibitor 3", Biol. Chem. Hoppe-Seyler 368:1427-1433, 1987.

(Continued)

*Primary Examiner* — Peter J Reddig
(74) *Attorney, Agent, or Firm* — Fish & Richardson P.C.

(57) ABSTRACT

The present invention provides anti-cancer agents comprising protein C inhibitor (PCI) or derivatives thereof as an active ingredient. The anti-cancer agents of the present invention have activities of suppressing cancer cell growth, and cancer metastasis, infiltration, and angiogenesis. Further, the present invention has shown that derivatives containing a heparin-binding domain of PCI inhibit the growth, metastasis and angiogenesis of cancer cells. Therefore, according to the present invention, PCI or derivatives thereof are useful for inhibiting the growth, metastasis and angiogenesis of cancer.

7 Claims, 13 Drawing Sheets

OTHER PUBLICATIONS

Stump et al., "Purification and characterization of a novel inhibitor of urokinase from human urine", The Journal of Biological Chemistry 261(27):12759-12766, 1986.

Suzuki et al., "Protein C inhibitor", The Journal of Biological Chemistry 258(1):163-168, 1983.

Suzuki et al., "Characterization of a cDNA for human protein C inhibitor", The Journal of Biological Chemistry 262(2):611-616, 1987.

Fair and Marlar, "Biosynthesis and Secretion of Factor VII, Protein C, Protein S, and the Protein C Inhibitor From a Human Hepatoma Cell Line," *Blood*, 67(1):64-70 (1986).

Hamada et al., "Protein C inhibitor regulates hepatocyte growth factor activator-mediated liver regeneration in mice," *Gut*, 57:365-373 (2008).

Japanese Patent Office, International Search Report for App. Ser. No. PCT/JP2005/018675, mailed Nov. 8, 2005, 2 pages.

International Preliminary Report on Patentability for App. Ser. No. PCT/JP2005/018675, dated Apr. 17, 2007, 5 pages.

USPTO Restriction Requirement in U.S. Appl. No. 11/577,157, dated Jul. 22, 2009, 7 pages.

European Search Report for App. Ser. No. EP 05 79 3705, dated Feb. 12, 2009, 5 pages.

Japanese Patent Office, International Search Report for App. Ser. No. PCT/JP2006/308095, mailed Jul. 25, 2006, 5 pages.

International Preliminary Report on Patentability for App. Ser. No. PCT/JP2006/308095, dated Oct. 23, 2007, 6 pages.

Fish & Richardson P.C., Response to Restriction Requirement dated Jul. 22, 2009 in U.S. Appl. No. 11/577,157, filed Oct. 14, 2009, 2 pages.

USPTO Restriction Requirement in U.S. Appl. No. 11/577,157, dated Dec. 31, 2009, 5 pages.

Fish & Richardson P.C., Response to Restriction Requirement dated Dec. 31, 2009 in U.S. Appl. No. 11/577,157, filed Feb. 24, 2010, 1 page.

USPTO Non-Final Office Action in U.S. Appl. No. 11/577,157, dated May 27, 2010, 23 pages.

Nishioka et al., "The Role of the COOH-terminal Region of Antithrombin III," J. Biol. Chem., 267(31):22224-22229 (1992).

Hayashi et al., "Gene organization of human protein C inhibitor, a member of SERPIN family proteins encoded in five exons," Int. J. Hematol., 58:213-224 (1993).

Andreasen et al., "The urokinase-type plasminogen activator system in cancer metastasis: a review," *Int. J. Cancer*, 72(1):1-22 (1997).

Cao et al., "Expression of protein C inhibitor (PCI) in benign and malignant prostatic tissues," *Prostate*, 57(3):196-204 (2003).

Palmieri et al., "Plasminogen activator inhibitor-1 and -3 increase cell adhesion and motility of MDA-MB-435 breast cancer cells," *J. Biol. Chem.*, 25:277(43):40950-7 (2002).

Suzuki et al., "Protein C and its inhibitor in malignancy," *Semin. Thromb. Hemost.*, 33(7):667-72 (2007).

Suzuki, K., "The multi-functional serpin, protein C inhibitor: beyond thrombosis and hemostasis," *J. Thromb. Haemost.*, 6(12):2017-26 (2008).

Yoshikawa et al., "Protein C inhibitor suppresses tumor cell growth and metastasis by inhibiting angiogenesis," retrieved from the Internet: http://www.ors.org/web/Transactions/52/1849.pdf; $52^{nd}$ Annual Meeting of the Orthopaedic Research Society, Paper No. 1849 (Jan. 15, 2009).

\* cited by examiner

ANTI-CANCER AGENT COMPRISING PROTEIN C INHIBITOR

CROSS-REFERENCE TO RELATED APPLICATIONS

This application is the National Stage of International Application No. PCT/JP2006/308095, filed on Apr. 18, 2006, which claims the benefit of Japanese Patent Application Serial No. 2005-120083, filed on Apr. 18, 2005. The contents of both foregoing applications are hereby incorporated by reference in their entireties.

TECHNICAL FIELD

The present invention relates to anti-cancer agents. More specifically, the present invention relates to anti-cancer agents comprising protein C inhibitor, therapeutic methods using anti-cancer agents comprising protein C inhibitor, and methods for manufacturing anti-cancer agents comprising protein C inhibitor.

BACKGROUND

Recently, a major cause of death in advanced countries has shifted from infectious diseases to adult diseases. In the midst of such change in the disease structure cancer is a particularly important disease that commonly ranks high among the major causes of death in many countries. In Japan, for example, the annual number of people who die from cancer is over 300,000. This is nearly twice as high as the number of people who die from heart diseases. Therefore, it is an important research challenge to provide cancer therapeutic technology.

Generally, surgical treatment, physicochemical treatment, drug treatment and the like are used for cancer therapy. Physicochemical treatment includes radiation therapy, particle beam (heavy charged particle beam) therapy, and thermotherapy. Many chemotherapeutic agents used for drug treatment have been put into practical use. Further, therapeutic effects of new approaches such as vaccine therapy and cellular immunotherapy have been confirmed. However, it is still an important research challenge to provide methods for treating cancer. In particular, techniques to prevent malignant transformation of cancer or methods to treat malignant cancer will contribute greatly to the medical treatment of cancer if they can be provided.

Generally, the mechanisms of malignant cancer transformation can be explained by growth, infiltration, and metastasis of cancer cells. In other words, when grown cancer cells metastasize by infiltration, the cancer is regarded as malignant. Cancer growth usually involves angiogenesis. Therefore, angiogenesis is also an important mechanism underlying malignant cancer transformation.

A series of the underlying mechanisms of malignant cancer transformation are explained in general as follows. First, cancer cells are grown and released from a primary site. The released cancer cells travel through lymphatic flow and blood flow and infiltrate other tissues. Metastasis is established when the infiltrated cancer cells start growing again. The growth of cancer cells requires angiogenesis. Angiogenesis also has great significance in the release of cancer cells from a primary site into the blood flow. It is considered that if any of these mechanisms is inhibited, the malignant transformation of cancer can be prevented. Thus, cell growth, infiltration, metastasis, and angiogenesis are important therapeutic targets in the treatment of cancer, especially of malignant cancer.

More than 90% of cancer occurs in epithelial cells. Epithelial cells maintain a strong sheet structure by adhering to one another through E-cadherin. Therefore, migration of epithelial cells is restricted. In malignant cancer, the easy release from a primary site is attributed to the weak intercellular adhesiveness of cancer.

However, malignant transformation cannot be explained only by migration property of cells. Generally, solid cancer tissues are wrapped in an extracellular matrix (ECM). In order for cancer to metastasize, cancer cells should pass through the ECM by certain mechanisms. ECM is mainly composed of the following components: collagen, fibronectin, laminin, proteoglycan, and elastin.

The percentage of each component and other components differs from tissue to tissue. Furthermore, each of these components has some subtypes. However, the most essential component of ECM that is common to multiple tissues is collagen. It has been revealed that malignant cancer migrates within tissues by producing an enzyme that degrades the collagen in ECM. Generally, collagen is a stable molecule and often possesses resistance to various proteases. Therefore, destruction of ECM by protease is an important condition for cancer to be malignant. A number of proteases involved in the decomposition of ECM have been identified. Proteases that participated in the decomposition of ECM are referred to as matrix metalloproteinases (MMPs). MMPs are seen as an important target molecule for inhibiting cancer metastasis. In the living body, protease inhibitors such as tissue inhibitor of metalloproteinase (TIMP) and α-2-macroglobulin (α2M) control the activity of MMPs.

Meanwhile, some MMPs change from a latent form to an active form upon digestion by another protease. For example, MMP-1 and MMP-3 are known to become an active form with plasmin. Plasmin acquires protease activity through the activation of plasminogen which requires the plasminogen activator (PA). There are two types of PA: urokinase type (uPA) and tissue type (tPA). tPA is a molecule that acts mainly on fibrinolytic system and is used as a thrombolytic agent. On the other hand, it has been pointed out that uPA may be involved in the infiltration and metastasis of cancer.

As discussed above, angiogenesis is an important mechanism underlying the malignant transformation of cancer. Therefore, like MMPs, angiogenesis in cancer tissues is also considered an important target in cancer therapeutic strategy. In fact, it is known that the expression of vascular endothelial growth factor (VEGF) is elevated in many cancers. Furthermore, it has been pointed out that the ECM-decomposing proteases have an important role not only in the cell migration as described above but also in angiogenesis. For example, proteases decompose ECM to make room for angiogenesis. As described above, various protease activity control systems are intricately involved in the malignant transformation of cancer.

In the living body, protease activities are generally controlled by the binding of proteases to their inhibitors. Furthermore, the function of some protease activating factors such as PA is also controlled by their inhibitors. For example, it has been shown that uPA as described above forms a complex with protein C inhibitor (PCI) in urine (Non-Patent Document 1). It is also known that PCI inhibits the activity of uPA (Non-Patent Document 2).

PCI is a protease inhibitor identified as an inhibitory factor of protein C, which is an anticoagulant protease (Non-Patent Documents 3 and 4). It belongs to the serine protease inhibitor (SERPIN) family, and has been found to have inhibitory activities against thrombin, factor Xa, factor XIa, plasma kallikrein, uPA, and the like. Plasminogen activator inhibitor 3, which was identified as an inhibitor of PA, is the same molecule as PCI.

[Non-Patent Document 1] Stump D. C. et al., J. Biol. Chem. 261: 12759-66, 1986

[Non-Patent Document 2] Stief T. W. et al., Biol. Chem. Hoppe Seyler 368: 1427-33, 1987

[Non-Patent Document 3] Marlar R. A. et al., J. Clin. Invest. 66: 1186-9, 1980

[Non-Patent Document 4] Suzuki K. et al., J. Biol. Chem. 258: 163-8, 1983

SUMMARY

Problems to be Solved by Invention

An objective of the present invention is to provide anti-cancer agents. Another objective of the present invention is to provide anti-cancer agents that have inhibitory activities against cell growth, metastasis and angiogenesis in cancer. The present invention also relates to therapeutic methods using the anti-cancer agents and methods of producing the anti-cancer agents.

Means for Solving the Problems

Based on the fact that the expression of PCI was significantly decreased in renal cancer tissues, the present inventors associated the decreased PCI expression with the occurrence of renal cancer and growth of renal cancer cells, and examined effects of PCI on the infiltration and metastasis of renal cancer cells. Then, they have revealed that PCI inhibits the infiltration of renal cancer cells into Matrigel (in vitro) (Wakita T. et al., Int. J. Cancer 108: 516-23, 2004). In addition, it has been reported that cell adhesion molecules are increased in breast cancer cells that overexpress PCI (Palmieri D. et al., J. Biol. Chem. 277: 40950-7, 2002). In order to confirm these effects of PCI on cancer cells in vivo, the present inventors examined the effects of PCI on the growth and metastasis of Caki-1 renal cancer cells. However, the Caki-1 cells used in the experiment did not survive in SCID mice (Wakita T. et al., Int. J. Cancer 108: 516-23, 2004). Therefore, it is still unknown as to how PCI actually acts against renal cancer in vivo.

Therefore, the present inventors carried out studies using MDA-231 breast cancer cells instead of the Caki-1 cells, and successfully showed effects of PCI on cancer cells in vivo. Further, they demonstrated that PCI has an activity of inhibiting the growth and metastasis of cancer cells in vivo, and thereby completed the present invention. Moreover, they discovered that part of the PCI anti-cancer effect in vivo does not depend on its protease inhibiting activity, and thereby completed the present invention. Specifically, the present invention is to provide the following anti-cancer agents:

[1] an anti-cancer agent comprising protein C inhibitor or a derivative thereof as an active ingredient;
[2] the anti-cancer agent of [1], wherein the agent suppresses at least one activity selected from cancer growth, cancer metastasis, and angiogenesis;
[3] the anti-cancer agent of [1] or [2], wherein the cancer is breast cancer;
[4] the anti-cancer agent of [2], wherein the protein C inhibitor derivative has a lower protease inhibitory activity than the protein C inhibitor;
[5] the anti-cancer agent of [4], wherein the protein C inhibitor derivative is a protein comprising a heparin-binding domain of the protein C inhibitor;
[6] the anti-cancer agent of [5], wherein the protein C inhibitor derivative is a protein capable of binding to either or both of heparin and heparin-like glycosaminoglycan;
[7] the anti-cancer agent of [1], wherein the agent suppresses cancer infiltration; and
[8] the anti-cancer agent of [7], wherein the protein C inhibitor derivative has a protease inhibitory activity.

Alternatively, the present invention relates to the use of protein C inhibitor or derivatives thereof in the manufacture of anti-cancer agents. The present invention also relates to the use of protein C inhibitor or derivatives thereof in the treatment of cancer. Additionally, the present invention relates to methods for treating cancer which comprise administering protein C inhibitor or derivatives thereof. Specifically, the present invention provides the following:

[9] a method for treating cancer, comprising the step of administering protein C inhibitor or a derivative thereof;
[10] the method of [9], wherein at least one activity selected from cancer growth, cancer metastasis, and angiogenesis is suppressed;
[11] the method of [9] or [10], wherein the cancer is breast cancer;
[12] the method of [10], wherein the protein C inhibitor derivative has a lower protease inhibitory activity than the protein C inhibitor;
[13] the method of [12], wherein the protein C inhibitor derivative is a protein comprising a heparin-binding domain of the protein C inhibitor;
[14] the method of [13], wherein the protein C inhibitor derivative is a protein capable of binding to either or both of heparin and heparin-like glycosaminoglycan;
[15] the method of [9], wherein cancer infiltration is suppressed;
[16] the method of [15], wherein the protein C inhibitor derivative has a protease inhibitory activity;
[17] use of protein C inhibitor or a derivative thereof as an active ingredient for manufacturing an anti-cancer agent;
[18] the use of [17], wherein the anti-cancer agent suppresses at least one activity selected from cancer growth, cancer metastasis, and angiogenesis;
[19] the use of [17] or [18], wherein the cancer is breast cancer;
[20] the use of [18], wherein the protein C inhibitor derivative has a lower protease inhibitory activity than the protein C inhibitor;
[21] the use of [20], wherein the protein C inhibitor derivative is a protein comprising a heparin-binding domain of the protein C inhibitor;
[22] the use of [21], wherein the protein C inhibitor derivative is a protein capable of binding to either or both of heparin and heparin-like glycosaminoglycan;
[23] the use of [17], wherein the anti-cancer agent suppresses cancer infiltration; and
[24] the use of [23], wherein the protein C inhibitor derivative has a protease inhibitory activity.

Alternatively, the present invention provides cancer cell growth-suppressing agents, cancer metastasis-suppressing agents, cancer infiltration-inhibiting agents, and agents for inhibiting angiogenesis in cancer tissues, which all comprise PCI or derivatives thereof as an active ingredient. Furthermore, the present invention relates to uses of PCI or derivatives thereof in the manufacture of cancer cell growth-suppressing agents, cancer metastasis-suppressing agents, cancer infiltration-inhibiting agents, and agents for inhibiting angiogenesis in cancer tissues.

In addition, the present invention relates to uses of PCI or derivatives thereof in suppression of cancer cell growth, suppression of cancer metastasis, inhibition of cancer infiltration, and inhibition of angiogenesis in cancer tissues. Further, the present invention relates to methods of suppressing cancer cell growth, suppressing cancer metastasis, inhibiting cancer infiltration, or inhibiting angiogenesis in cancer tissues, which all comprise administering PCI or a derivative thereof.

Effects of the Invention

The present invention provides anti-cancer agents comprising PCI or a derivative thereof as an active ingredient. The present invention has shown that PCI suppresses cancer infiltration in a manner that depends on its protease inhibitory activity. Therefore, PCI derivatives having protease inhibitory activity are useful as inhibitors of cancer infiltration. On the other hand, the angiogenesis inhibitory activity of PCI in cancer does not depend on its protease inhibitory activity. Similarly, the cancer cell growth inhibitory activity of PCI does not depend on its protease inhibitory activity either. Accordingly, PCI derivatives whose protease inhibitory activity is low or deleted are useful as angiogenesis inhibitory agents and cancer cell growth-suppressing agents. It is a novel finding by the present invention that PCI derivatives lacking protease inhibitory activity suppress angiogenesis and cell growth.

Side effects due to the protease inhibitory activity can be prevented by using PCI derivatives having low or no protease inhibitory activity. For example, PCI has a strong inhibitory activity against the fibrinolytic system. Therefore, there is a concern that the fibrinolytic system may be inhibited by administration of PCI. However, by using PCI derivatives that lack protease inhibitory activity according to the present invention, it is possible to prepare agents having no inhibitory activity against the fibrinolytic system but retaining anti-cancer effect at the same time.

Moreover, PCI may inhibit activated protein C (APC) which has anticoagulant activity and anti-inflammatory activity, thereby inhibiting the coagulation control system and the inflammation control system in the living body. Similarly, PCI may inhibit the thrombin-thrombomodulin complex which exhibits the anticoagulation activity, and thereby inhibit the conversion of protein C to APC, lowering APC production. However, the use of PCI derivatives lacking protease inhibitory activity would solve these concerns, and enable one to prepare anti-cancer agents that do not affect the coagulation and inflammation control systems but retain the anti-cancer effect at the same time.

Further, endogenous proteins such as angiostatin and endostatin that have angiogenesis inhibitory activity are known. These endogenous angiogenesis inhibitory substances have strong angiogenesis inhibitory activity. Development of anti-cancer agents that target the angiogenesis activity of cancer using the above inhibitory activity is under progress. These endogenous angiogenesis inhibitory factors are considered to be produced through the digestion of plasmin or collagen by certain proteases. While protease inhibitors are effective as anti-cancer agents, they may inhibit the production of these angiogenesis inhibitory factors. The present invention can provide anti-cancer agents that do not have protease inhibitory activity. Specifically, the present invention provides anti-cancer agents that do not affect the production of endogenous angiogenesis inhibitors.

Kallistatin, which is a heparin-binding serpin, has been shown to have suppression effect on cancer cell growth that accompanies angiogenesis (Miao R. Q. et al., Blood 100: 3245-52, 2002). The inhibitory activity of kallistatin against angiogenesis of cancer cells is presumed to result from inhibition of the binding of VEGF with heparin which is important for the binding between VEGF and its receptor (Miao R. Q. et al., Am. J. Physiol. Cell Physiol. 284: C1604-13, 2003). It is also known that antithrombin (AT), which is also a heparin-binding serpin, has angiogenesis inhibitory activity (O'Reilly M S et al., Science 285: 1926-8, 1999). In the present invention, a mechanism independent of the protease inhibitory activity of PCI, that is, a mechanism different from those of the above reports, has been confirmed. The protease inhibitory activity-independent PCI anti-cancer effect is unexpectable from the known findings.

BRIEF DESCRIPTION OF THE DRAWINGS

In FIGS. 3A to 3D, untransfected MDA-231 cells ($2\times10^5$) were suspended in 500 μl DMEM in the presence of various concentrations of PCI (A), anti-human uPA IgG (B), PAI-1 (C), or uPA (D), and placed in a culture insert (upper chamber). The lower chamber contained 750 μl of 10% FBS-DMEM as a chemoattractant. After 24 hours of incubation, infiltrating cells on the lower surface of the membrane were fixed and stained. The cells were counted under a light microscope at 100-fold magnification. Data are shown as the number of cells (mean±S.D.) derived from four independent infiltration membranes. ND indicates "not detected".

FIG. 3B presents a graph showing the effect of anti-human uPA IgG on the infiltration activity of untransfected MDA-231 cells.

FIG. 3C presents a graph showing the effect of PAI-1 on the infiltration activity of untransfected MDA-231 cells.

FIG. 3D presents a graph showing the effect of uPA on the infiltration activity of untransfected MDA-231 cells.

DETAILED DESCRIPTION

Figure 1:
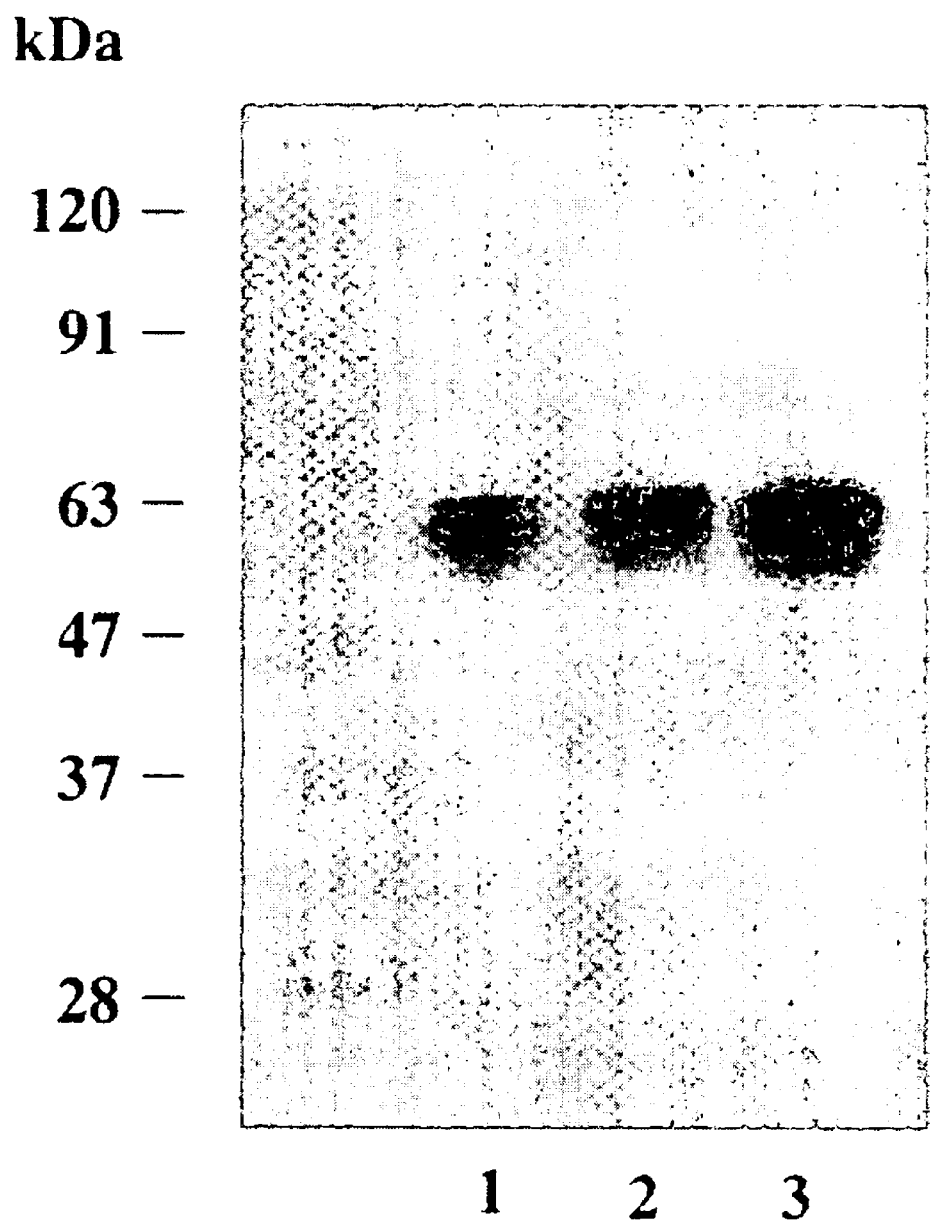
FIG. 1 is a photograph showing the Western blot analysis of recombinant intact PCI, R354APCI, and degPCI. 1 μg of each recombinant protein (lane 1, intact PCI; lane 2, R354APCI; lane 3, degPCI) was applied to SDS-PAGE and Western blotting using anti-human PCI rabbit IgG and then alkaline phosphatase-linked anti-rabbit IgG. As described in Materials and Methods, each band was visualized using the Western Blue Stabilized Substrate.

The present inventors have discovered that PCI shows anti-cancer effect in vivo. The anti-cancer effect of PCI has been found to result from suppression of the growth, infiltration and angiogenesis of cancer cells. Further, a number of PCI derivatives that retain anti-cancer effect are shown. Based on these findings, anti-cancer agents containing PCI or a derivative thereof as an active ingredient are provided.

PCI is a single-chain glycoprotein with a molecular weight of approximately 57 kDa. PCI used in the present invention may be natural PCI or artificially produced PCI. Human PCI and other mammalian PCIs are known (Suzuki, K. et al., J. Biol. Chem. 262: 611-6, 1987). When used in treatment for humans, human-derived PCI is preferable. An amino acid sequence of human PCI is shown in SEQ ID NO: 2 (GenBank Accession Number: P05154), and a cDNA nucleotide sequence is shown in SEQ ID NO: 1.

In the present invention, PCI derived from non-human animals may also be used. Specifically, known mammalian PCIs include, for example, mouse, rat, and bovine PCIs (Zechmeister-Machhart, M. et al., Gene 186(1): 61-6, 1997; Wakita, T. et al., FEBS Lett. 429 (3): 263-8, 1998; Yuasa, H. et al., Thromb. Haemost. 83(2): 262-7, 2000).

In the present invention, polypeptides comprising full-length PCI and polypeptides comprising a fragment sequence thereof may be used as long as they have anti-cancer effect. In the present invention, polypeptides comprising a fragment PCI sequence and retaining anti-cancer effect are referred to as PCI derivatives. Polypeptides comprising full-length PCI and polypeptides comprising a fragment sequence thereof include fusion polypeptides modified with other peptides. Hereinafter, the term "PCIs" is used to encompass PCI as well as their derivatives that retain anti-cancer effect.

The present invention has shown that the metastasis and growth activities of cancer cells do not depend on the protease inhibitory activity of PCI. Therefore, PCI fragments which have low or no protease inhibitory activity may be used as an active ingredient in anti-cancer agents for suppressing both or either cancer metastasis and growth. In the present invention, the low protease inhibitory activity refers to, for example, a protease inhibitory activity of 50% or less, 30% or less, or normally 10% or less than that of natural PCI.

The inhibitory activity of PCI derivatives against proteases may be evaluated by methods shown in the Examples, for example. Specifically, activated protein C (APC) is incubated with a PCI derivative whose inhibitory activity is to be evaluated. The protease inhibitory activity of PCI or the derivative thereof can be evaluated by comparing the post-incubation protease activity. The protease activity can be measured by adding an appropriate substrate and using the quantity of substrate digested by the protease or the digestion rate as an index. Digestion can be optically monitored using a chromogenic substrate obtained by binding a dye to a peptide. In the Examples, Glu-Pro-Arg-p-nitroanilide (S-2366) was used as a chromogenic substrate.

The aPC (activated protein C) used for evaluating protease inhibitory activity may be synthesized chemically or by using genetic engineering techniques. Not only full-length aPC amino acid sequences, but also fragments retaining the aPC enzymatic activity may be used. Amino acid sequences of human and other mammalian aPCs are known (Mather, T. et al., EMBO J. 15: 6822-6831, 1996; Foster, D. C. et al., Proc. Natl. Acad. Sci. 82: 4673-4677, 1985). For example, a commercially available aPC (protein C activated, from human plasma, SIGMA, #P2200) may be used.

Examples of the PCI derivatives which have a low protease inhibitory activity include polypeptides described below. Polypeptides having these features are useful as an active ingredient of the anti-cancer agents of the present invention.

(a) PCI fragments containing an amino acid sequence constituting the heparin-binding domain
(b) Mutant PCI having a mutation at the site of aPC digestion Next, useful PCI derivatives in the present invention will be specifically described. In the present invention, PCI variants lacking protease inhibitory activity include, for example, polypeptides containing a domain of PCI that binds to heparin or heparin-like glycosaminoglycans. For example, domains in the human PCI amino acid sequence listed below are considered important for binding with heparin (Kuhn L. A. et al., Proc. Natl. Acad. Sci. USA. 87: 8506-8510, 1990). Homologous domains can be identified in PCIs derived from a non-human animal by amino acid sequence alignment. Therefore, PCI fragments containing such domains may be used as PCI derivatives in the present invention. Such fragments may include, for example, those containing amino acid residues 1-354 at the N terminus. The fragment named degPCI in the Examples (SEQ ID NO: 15) is an amino acid sequence corresponding to positions 1-354 of SEQ ID NO: 2, which has been found to have no protease inhibitory activity but shows sufficient anti-cancer effect.

Positions 1-15 (helix A)
Positions 264-278 (helix H)

Examples of heparin-like glycosaminoglycans that bind to PCI are shown in Table 1 along with their structures. Table 1 also shows the in vivo distribution of these heparin-like glycosaminoglycans. PCI derivatives that bind with these glycosaminoglycans are useful in the present invention.

TABLE 1

| Name | Basic Structure | Distribution |
| --- | --- | --- |
| Hyaluronic acid | GlcUAβ1-3GlcNAc | vitreous body, joint fluid, umbilical cord |
| Keratan sulfate | Galβ1-4GlcNAc | cartilage, interspinal disk, cornea |
| Heparan sulfate | GlcUAα1-4GlcNAc, IdoAα1-4GlcNAc | cell surface, basal membrane |
| Heparin | GlcUAα1-4GlcNAc, IdoAα1-4GlcNAc | small intestine, muscle, lung, spleen, tendon, liver, mast cell |
| Chondroitin | GlcUAβ1-3GalNAc | cornea |
| Chondroitin sulfate | GlcUAβ1-3GalNAc | bone, dentine, cartilage |
| Dermatan sulfate | GlcUAβ1-3GalNAc, IdoAβ1-3GalNAc | skin, artery wall, tendon, bone, dentine |

Among them, chondroitin sulfate has a strong activity in enhancing the PCI activity. Alternatively, dextran sulfate is also known to enhance the PCI activity like heparin (Kazama Y. et al., Thromb. Res. 48(2): 179-85, 1987 Oct. 15). Therefore, PCI variants retaining the ability to bind to chondroitin sulfate or dextran sulfate are preferred in the present invention.

The ability of PCI derivatives to bind with heparin or heparin-like glycosaminoglycans may be evaluated by any methods. Hereinafter, the term "heparins" is used to indicate heparin and heparin-like glycosaminoglycans. For example, the binding between PCI derivatives and heparins may be evaluated by observing binding of the PCI derivatives with fixed heparins. For example, heparin columns can be used to compare the binding of PCI derivatives with heparin. Specifically, PCI or PCI derivatives are adsorbed to heparin agarose columns and then eluted with NaCl. The PCI or PCI derivatives contained in the eluted fractions are quantified using ELISA or the like to compare the levels of column adsorption. PCI or PCI derivatives having a higher heparin adsorption activity are eluted in later fractions (Kuhn L. A. et al., Proc. Natl. Acad. Sci. USA. 87: 8506-8510, 1990).

The PCI derivative used in the present invention may also be a PCI mutant having a mutation at the aPC digestion site. In the process in which PCI binds to and thereby inactivates aPC, PCI is digested by aPC in a region near its C terminus and the C-terminal fragment is released. The aPC digestion site has shown to be between Arg and Ser at positions 354 and 355 (Suzuki K. et al., J. Biol. Chem. 262(2): 611-616, 1987). PCI derivatives containing a mutation in this region are not digested by aPC lose their protease inhibitory activity. For example, the PCI mutant R354APCI shown in the Examples is a PCI derivative in which Arg at position 354 is mutated to Ala. Although R354APCI retains the heparin-binding ability in the N-terminal region, it does not have protease inhibitory activity since it contains a mutation at the aPC digestion site. Such mutants can be used as PCI derivatives in the present invention.

In the present invention, PCI may be human polypeptides comprising the amino acid sequence of SEQ ID NO: 2 or polypeptides derived from various non-human species. The PCI derivative in the present invention may be polypeptides comprising an amino acid sequence in which one or more amino acid residues are modified in the amino acid sequence of PCI, as long as they have anti-cancer effect. Modifications of the amino acid sequence may be deletion, replacement, or addition of one or more amino acids in the amino acid sequence. For example, a PCI amino acid sequence may be modified so as to improve its stability or physical and biological properties in vivo. Methods for modifying amino acid sequences are known. For example, site-directed mutagenesis (see Kunkel T. A., Proc. Natl. Acad. Sci. USA 82: 488-92, 1985), PCR-based mutagenesis, cassette mutagenesis, and the like can be used to obtain polypeptides with modified amino acid sequences or DNAs encoding the same.

Such mutants comprise an amino acid sequence which is at least 70% identical to the original amino acid sequence, more preferably at least 75%, even more preferably at least 80%, still more preferably at least 85%, yet more preferably at least 90%, and most preferably at least 95% identical. Herein, sequence identity is defined as the percentage of residues identical to those in the original amino acid sequence of PCI, determined after the sequences are aligned and gaps are appropriately introduced to maximize the sequence identity as necessary.

When modifying an amino acid residue, it is possible to maintain the property of a protein by substituting the residue with another amino acid residue that conserves the property of its amino acid side chain. For example, amino acids having the following property have similar features to one another, and the protein activity is likely to be maintained when they are replaced with one another. The letters within parentheses indicate one-letter amino acid codes.

hydrophobic amino acids (A, I, L, M, F, P, W, Y, V)
hydrophilic amino acids (R, D, N, C, E, Q, G, H, K, S, T)
amino acids having aliphatic side chains (G, A, V, L, I, P)
amino acids having hydroxyl group-containing side chains (S, T, Y)
amino acids having sulfur atom-containing side chains (C, M)
amino acids having carboxylic acid- and amide-containing side chains (D, N, E, Q)
amino acids having base-containing side chains (R, K, H)
amino acids having aromatic-containing side chains (H, F, Y, W)

The substitution of amino acids within each group is called conservative substitution. It is well known that a polypeptide having a modified amino acid sequence in which one or more amino acid residues are deleted, added, and/or substituted with other amino acids in a certain amino acid sequence can retain its original biological activity (Mark, D. F. et al., Proc. Natl. Acad. Sci. USA 81: 5662-6, 1984; Zoller, M. J. and Smith, M., Nucleic Acids Res. 10: 6487-500, 1982; Wang, A. et al., Science 224: 1431-3, 1984; Dalbadie-McFarland, G. et al., Proc. Natl. Acad. Sci. USA 79: 6409-13, 1982). The number of amino acids to be mutated in the present invention is not particularly limited, but generally 40% or less of the amino acids constituting a full-length amino acid sequence, preferably 35% or less, and more preferably 30% or less (e.g., within 25%). The identity of amino acid sequences can be determined by methods described below.

Specifically, the identity of one nucleotide sequence or amino acid sequence to another can be determined using the algorithm BLAST, by Karlin and Altschul (Karlin S. and Altschul S. F., Proc. Natl. Acad. Sci. USA 90, 5873-7, 1993). Programs such as BLASTN and BLASTX were developed based on this algorithm (Altschul S. F. et al., J. Mol. Biol. 215, 403-10, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

In the present invention, PCI and derivatives retaining its anti-cancer effect may be used. The anti-cancer effect of PCI and PCI derivatives can be confirmed by, for example, method shown in the Examples. Specifically, the following methods can be used to confirm the effects on cancer cell activities such as infiltration, growth, metastasis, and angiogenesis. The anti-cancer effect of a candidate polypeptide can be confirmed by these methods, and a polypeptide that has been confirmed to have anti-cancer effect on at least one of infiltration, growth, metastasis, and angiogenesis may be selected as a PCI derivative of the present invention. The anti-cancer effect may be evaluated by comparing the polypeptide with a control polypeptide having no anti-cancer effect. When evaluating anti-cancer effect using a vector carrying a DNA encoding the polypeptide, it is also possible to use the vector not containing the DNA (mock) as a control. Alternatively, when a polypeptide known to have anti-cancer effect is used as a control, it is possible to confirm whether a candidate polypeptide has an equal or higher anti-cancer effect than the control.

[Invasion: In Vitro Invasion Assay]

Invasion of cancer cells can be observed in Matrigel. The effect of a PCI derivative on cancer cell invasion can be determined by incubating cancer cells with the PCI derivative.

[Growth: Evaluation of Tumor Growth in Vivo]

The effect of a PCI derivative on cancer cell growth can be evaluated by observing the growth of cancer cells transformed with a DNA encoding the PCI derivative. The breast cancer cell line MDA-231, for example, may be used as the cancer cell. The effect on cancer cell growth in vivo can be evaluated by transplanting cancer cells into SCID mice.

[Metastasis: Assay of Experimental Lung Metastasis]

It is also possible to evaluate the effect of a PCI derivative on cancer cell metastasis using an in vivo evaluation system. For example, MDA-231 breast cancer cells can be inoculated into an SCID mouse at the caudal vein to observe the metastasis of the cells to the lung. If the metastasis to the lung is suppressed by transformation with a DNA encoding the PCI derivative, the inhibitory activity of the PCI derivative against metastasis can be confirmed.

[Angiogenesis: Matrigel Implant Assay]

The effect of a PCI derivative on angiogenesis in cancer tissues can also be evaluated in vivo. Specifically, Matrigel containing cancer cells is implanted into SCID mice, and the angiogenesis activity of the cancer cells can be evaluated using the entry of blood components into the Matrigel as an index. In the Examples, the Matrigels were digested and hemoglobin contents in the Matrigels were compared. If angiogenesis is suppressed in cancer cells transformed with a DNA encoding the PCI derivative, the inhibitory activity of the PCI derivative against angiogenesis can be confirmed.

[Angiogenesis: Chicken Chorioallantoic Membrane Assay (CAM-Assay)]

By culturing cancer cells on a chicken chorioallantoic membrane and observing angiogenesis on the chorioallantoic membrane, the angiogenesis activity of the cancer cells can be evaluated. If angiogenesis is suppressed in the cancer cells transformed with a DNA encoding the PCI derivative, the inhibitory activity of the PCI derivative against angiogenesis can be confirmed.

[Angiogenesis: In Vitro Angiogenesis Assay]

The angiogenesis activity of cancer cells can be evaluated using as an index capillary vessels formed by the cancer cells in the Matrigel when they are cultured in the Matrigel (Schnaper H. W. et al., J. Cell Physiol. 65: 107-18, 1995). If angiogenesis is suppressed in the cancer cells transformed with a DNA encoding the PCI derivative, the inhibitory activity of the PCI derivative against angiogenesis can be confirmed.

In the present invention, cancer cell activities such as growth, infiltration, metastasis, and angiogenesis can be evaluated in vivo by using MDA-231 breast cancer cells as the cancer cell. Specifically, the mechanisms of malignant cancer transformation such as growth, infiltration, metastasis, and angiogenesis can be experimentally replicated by implanting MDA-231 into SCID mice. Therefore, the present invention provides a method for evaluating the anti-cancer effect of a test substance, comprising the steps of:

a) implanting MDA-231 breast cancer cells into immunodeficient animals;

b) contacting a test substance with MDA-231 before, simultaneously with, or after the implantation of a);

c) measuring the cancer cell activity of MDA-231; and d) comparing the activity measured in c) with a control, wherein the anti-cancer effect of the test substance is detected when the activity is lower than the control.

In the present invention, cancer cell activity may be selected from the group consisting of growth, infiltration, metastasis, and angiogenesis of cells. These activities can be measured using the above-described methods, for example. Meanwhile, the MDA-231 cells used in the above methods are available as MDA-MB-231 from cell banks (ATCC Accession No. HTB-26).

PCIs may be isolated based on its physical properties and the like from natural sources such as blood, urine, seminal plasma, synovial fluid, or cells or tissues expressing PCIs. Alternatively, PCIs may be chemically synthesized based on known sequence information. PCI derivatives may be synthesized using genetic engineering techniques by expressing DNAs encoding an amino acid sequence of interest. Specifically, host cells can be transformed using a gene encoding PCI or PCI derivative by using genetic recombination techniques. The gene is preferably inserted into an appropriate expression vector before host cell transformation. By culturing the resultant transformed cells, the PCI or PCI derivative may be obtained from the cells or culture supernatants thereof. Recombinant PCIs or PCI derivatives may be prepared, for example, as described in the Examples.

Vectors suitable for producing PCI or PCI derivatives using genetic engineering methods include various vectors using viruses, cosmids, plasmids, bacteriophages, and the like (Molecular Cloning $2^{nd}$ ed., Cold Spring Harbor Press (1989); Current Protocols in Molecular Biology, John Wiley & Sons (1987)). Such vectors can comprise appropriate regulatory sequences such that the PCI is expressed when introduced into desired host cells. The gene encoding PCI or a PCI derivative is inserted to the vector so as to maintain the correct reading frame relative to the regulatory sequence. The gene encoding PCI or PCI derivatives can be any types or have any nucleotide sequences as long as they can be expressed by the selected vector and host. In addition to DNAs, RNAs or the like may be used in some cases.

Preferred "regulatory sequences" for expression can be appropriately selected depending on host cells and vectors. Specifically, when the host cell is a prokaryotic cell, the vector contains as regulatory sequences at least a promoter, a ribosome-binding site, and a terminator. Alternatively, when the host is a eukaryotic cell, the essential "regulatory sequences" are a promoter and terminator. The vector can also comprise, as necessary, an enhancer, splicing signal, transcription factor, transactivator, poly A signal, and/or polyadenylation signal, and so on.

The vectors for expressing PCI or PCI derivatives may also comprise selection markers if necessary. Such markers allow easy selection of transformed host cells. Furthermore, PCI or PCI derivative genes with signal peptide-encoding sequences attached may be inserted into vectors to translocate expressed cellular PCIs or PCI derivatives into the lumen of the endoplasmic reticulum or the extra-cellular space, or alternatively into the periplasm when the host cells are gram-negative bacteria. Such signal peptides may be original PCI signals or may be derived from different proteins, as long as they are properly recognized in selected host cells. Furthermore, linkers, start codons, stop codons, and such may be added, if required. For example, in 406 amino acid residues of the amino acid sequence of SEQ ID NO: 2, the N-terminal residues 1 to 19 are the signal sequence unique to human PCIs.

Genes can be inserted into vectors via ligase reactions using restriction enzyme sites (Molecular Cloning $2^{nd}$ ed., Cold Spring Harbor Press (1989) Section 5.61-5.63; Current Protocols in Molecular Biology, John Wiley & Sons (1987) 11.4-11.11). Such vectors may be designed by considering codon usage in the host cells to be used, and selecting nucleotide sequences that allow high efficiency expression (Grantham R. et al., Nucleic Acids Res. 9, r43-74, 1981).

When such vectors are introduced into adequate hosts, the above expression vectors and hosts can be used in combinations appropriate for producing PCI or PCI derivatives. Animal cells, plant cells, and fungal cells may be used as the eukaryotic host cells. Example of cells that can be used as hosts are listed below.

[Animal Cells]
(1) mammalian cells: for example, CHO, COS, myeloma, BHK (baby hamster kidney), HeLa, and Vero cells;
(2) amphibian cells: for example, *Xenopus oocytes;*
(3) insect cells: for example, Sf9, Sf21, and Tn5 cells, or silkworms.

[Plant Cells]
*Nicotiana* genus: for example, cells derived from *Nicotiana tabacum* are callus cultured.

[Fungal Cells]
Yeasts: for example, the *Saccharomyces* genus such as *Saccharomyces cerevisiae;*
Filamentous fungi: for example, the *Aspergillus* genus such as *Aspergillus niger.*

[Prokaryotic Cells]
Bacterial cells: for example, *Escherichia coli* and *Bacillus subtilis.*

PCI or PCI derivatives can be obtained by transferring a PCI gene or a PCI derivative gene into these cells using transformation, and then culturing the transformed cells in vitro.

Host cells can be transformed using methods suited to selected hosts and vectors. For example, when prokaryotic cells are used as the host, known methods include calcium treatment and electroporation. Examples also include the *Agrobacterium* method for plant cells, and the calcium phosphate precipitation method for mammalian cells. The present invention is not particularly limited to the methods described above. The present invention can use various known methods, including nuclear microinjection, cell fusion, electroporation, protoplast fusion, lipofectamine methods (GIBCO BRL), DEAE-dextran methods, and methods using FuGENE6 reagent (Boehringer-Mannheim).

Host cells can be cultured by known methods suited to selected cells. For example, when animal cells are used as the host, the cells may be cultured using a medium, such as DMEM, MEM, RPMI-1640, 199, or IMDM, if required, supplemented with fetal calf serum (FCS) and such, at a pH of about 6 to 8 at 30° C. to 40° C. for about 15 to 200 hours. In addition, if necessary, required treatments such as medium exchange, aeration, and stirring can be given during culture.

PCI or PCI derivatives are preferably used after purification by known methods. PCI or PCI derivatives can be purified to homogeneity by conventional protein purification methods. A desired protein can be separated and purified, for example, by appropriately selecting and combining the following purification techniques (Strategies for Protein Purification and Characterization, A Laboratory Course Manual, Daniel R. Marshak et al., eds., Cold Spring Harbor Laboratory Press (1996); Antibodies, A Laboratory Manual, Ed Harlow and David Lane, Cold Spring Harbor Laboratory (1988)):
chromatography column,
filter,
ultrafiltration,
salting out,
dialysis,
preparative polyacrylamide gel electrophoresis,
isoelectrofocusing, and the like.

The purification method in the present invention is not limited thereto. The chromatography available in the present invention includes:
affinity chromatography,
ion-exchange chromatography,
hydrophobic chromatography,
gel filtration,
reverse phase chromatography,
adsorption chromatography, and the like.

These chromatography methods can be conducted using liquid chromatography such as HPLC and FPLC. Affinity chromatography can be conducted, for example, using antibodies against PCI.

The anti-cancer agents of the present invention comprise PCI or PCI derivatives obtained as described above as an active ingredient. A single PCI or PCI derivative may be comprised as an active ingredient, or multiple PCIs and/or PCI derivatives may be comprised. The phrase "comprising PCI and/or PCI derivatives as an active ingredient" means comprising PCI and/or PCI derivatives as at least one active ingredient. The active ingredient content in an anti-cancer agent is not limited. Furthermore, the anti-cancer agents of the present invention may comprise other active ingredients having anti-cancer effect, in addition to PCI and/or PCI derivatives.

PCI and PCI derivatives can be formulated according to standard methods (see, for example, Remington's Pharmaceutical Science, latest edition, Mark Publishing Company, Easton, USA), and may comprise pharmaceutically acceptable carriers and/or additives. For example, carriers may include detergents (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the anti-cancer agents of the present invention may comprise other appropriate conventional carriers.

Specifically, such carriers include light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The agents may also comprise other low-molecular-weight polypeptides; proteins, such as serum albumin, gelatin, and immunoglobulin; and amino acids, such as glycine, glutamine, asparagine, arginine, and lysine.

When the agents are prepared as aqueous solutions for injection, PCI and/or PCI derivatives are dissolved in isotonic solutions comprising, for example, physiological saline, dextrose, and other adjuvants. The adjuvants include, for example, D-sorbitol, D-mannose, D-mannitol, and sodium chloride. In addition, appropriate solubilizing agents, such as alcohols (for example, ethanol), polyalcohols (for example, propylene glycol and PEGs), and non-ionic detergents (polysorbate 80 and HCO-50) may also be used in combination.

If necessary, PCI and/or PCI derivatives may be encapsulated in microcapsules (microcapsules made of hydroxymethylcellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for preparing sustained-release drugs are known (Langer et al., J. Biomed. Mater. Res. 15, 167-277, 1981; Langer, Chem. Tech. 12, 98-105, 1982; U.S. Pat. No. 3,773,919; European Patent Application (EP) No. 58,481; Sidman K. R. et al., Biopolymers 22, 547-56, 1983; EP No. 133,988). These known formulation techniques can be applied to the present invention.

The anti-cancer agents of the present invention can be administered either orally or parenterally, but are preferably administered parenterally. Specifically, the agents can be administered to patients by injection, nasally, transpulmonarily, and percutaneously. For example, injections can be administered systemically or locally by intravenous injection, intramuscular injection, intraperitoneal injection, or subcutaneous injection. Furthermore, the method of administration can be appropriately selected according to the age and symptoms of the patient. A single dose can be selected from between 0.0001 to 1,000 mg per kg of body weight. Alternatively, the dose can be selected from between 0.001 to 100,000 mg/body for each patient. However, the doses of the anti-cancer agents of the present invention are not limited to these examples.

Furthermore, the above-described genes encoding PCI and/or PCI derivatives may be incorporated in a gene therapy vector and prepared as an anti-cancer agent for gene therapy. Methods for administering the genes include direct injection using a naked plasmid, or packaging the genes in liposomes or such. Alternatively, a variety of gene therapy vectors may be used. For example, the following gene therapy viral vectors are known (see Adolph K. W. ed., Viral Genome Methods, CRC Press, Florida (1996)):

retroviral vectors,
adenovirus vectors,
vaccinia virus vectors,
poxvirus vectors,
adeno-associated virus vectors,
HVJ vectors, and the like.

Alternatively, the genes can be coated onto carrier beads such as colloidal gold particles (WO 93/17706 and such), and administered. However, methods of gene administration are not limited as long as the PCI or PCI derivative is expressed and allowed to exert its effect in vivo. Preferably, a sufficient dose may be administered by injecting or infusing the gene via a suitable parenteral route. The parenteral route includes intravenous, intraperitoneal, subcutaneous, intracutaneous, intra-adipose tissue, intra-mammary gland tissue, and intra-muscular routes, inhalation, gas-induced particle bombardment (using electron gulls and such), and via mucosa using, for example, nose drops. It is possible to administer a gene encoding PCI or PCI derivative by introducing the gene into cells ex vivo and return the cells into the animal. For the ex vivo introduction of the gene, liposome transfection, particle bombardment (U.S. Pat. No. 4,945,050), or viral infection may be used.

All prior art documents cited herein are incorporated herein by reference.

EXAMPLES

Materials and Methods (1) Materials

Restriction endonucleases were purchased from TOYOBO, Osaka, Japan. Taq DNA polymerase was from Roche Biochemicals (Basel, Switzerland). Klenow fragment, T4 polynucleotidekinase, and T4 DNA ligase were from NIPPON GENE (Tokyo, Japan). QuikChange XL Site-Directed Mutagenesis Kit was purchased from Stratagene (Cedar Creek, Tex., United States). The Dye Terminator Cycle Sequence Ready Reaction Kit was purchased from ABI, Foster City, Calif. Radioactive nucleotides ([$\alpha$-$^{32}$P]dCTP and [$\gamma$-$^{32}$P]ATP) were manufactured by Amersham Bioscience (Uppsala, Sweden). The transfection reagent Effectene was purchased from QIAGEN, Inc (Tokyo, Japan). All other chemicals and reagents used were of the highest grade commercially available.

2) Cell Culture

MDA-231 breast cancer cells were purchased from Japan Cancer Research Resources Bank. The MDA-231 cells were incubated at 37° C. in a humidified atmosphere containing 5% $CO_2$, in Dulbecco's Modified Eagle Medium (DMEM) (Nissui Pharmaceutical Co., Ltd., Tokyo, Japan) supplemented with 10% fetal bovine serum (FBS) (EQUITECH-BIO, Kerrville, Tex.), 100 µg/ml penicillin and 100 IU/ml streptomycin (Sanko Junyaku Co., Ltd., Tokyo, Japan).

3) Preparation of Cells Expressing Intact PCI, R354APCI, or degPCI

An expression vector of human intact PCI, R354APCI, or degPCI was constructed as follows. The cDNA of R354APCI having a signal peptide was prepared by the QuikChange Site-Directed Mutagenesis Kit (Stratagene, La Jolla, Calif.) using synthetic oligonucleotide primers consisting of the following nucleotide sequences, and full-length PCI cDNA (Suzuki K. et al., J. Biol. Chem. 262:611-6, 1987) as a template. The underlined nucleotide indicates a mutation site.

```
5'-TTCACTTTCGCGTCGGCCCGC-3'      (SEQ ID NO: 3)
and

5'-GCGGGCCGACGCGAAAGTGAA-3'      (SEQ ID NO: 4)
```

The cDNA of degPCI having a signal peptide sequence was prepared by polymerase chain reaction (PCR) (Saiki R. K. et al., Science 239: 487-91, 1998) using the following primer pair. The primers indicated by SEQ ID NO: 5 and SEQ ID NO: 6 correspond to positions 31 to 52 and 1194 to 1176 of the PCI cDNA, respectively (Hayashi T. et al., Int. J. Hematol. 58: 213-224, 1993). The underlined nucleotides indicate the EcoR I site inserted at the 5' termini of the two primers.

```
                                 (SEQ ID NO: 5)
5'-GCGAATTCCTCTGGCAGAGCCTCCGTTTCC-3'
and (SEQ ID NO: 6)
5'-GCGAATTCTCACCTGAAAGTGAAGATTGTCC-3'
```

Following the manufacturer's instructions, the DNA fragment of R354APCI or degPCI was subcloned into pcRII-TOPO, and *E. coli* Top10F' was transformed with the plasmid. The DNA sequences were confirmed using the ABI 310 genetic analyzer. Next, the human intact PCI cDNA (Suzuki K. et al., J. Biol. Chem. 262: 611-6, 1987), mutant R354APCI cDNA, or degPCI cDNA was inserted into the mammalian expression vector pRC/CMV (Invitrogen Corp., Carlsbad, Calif.) and transfected into MDA-231 by using an Effectene Transfection Reagent.

After transfection, cell lines expressing intact PCI, R354APCI and degPCI MDA-231 were selected using DMEM containing 800 μg/ml Geneticin. After that, the PCI antigen in the medium of each cell line was measured by an enzyme-linked immunosorbent assay (ELISA), and expression of intact PCI, R354APCI or degPCI in the cloned MDA-231 cell line was confirmed by Northern blot analysis that evaluates PCI mRNA as described below. From transfected 480 cell lines, MDA-PCI 1 and MDA-PCI 2 were selected as the cell lines expressing a large amount of PCI; MDA-R354APCI 1 and MDA-R354APCI 2 were selected as the cell lines expressing a large amount of R354APCI; and MDA-degPCI 1 and MDA-degPCI 2 were selected as the cell lines expressing a large amount of degPCI, and these were used in the experiments. Following a similar procedure, MDA231 cells prepared by transfecting pRC/CMV that does not contain an inserted DNA were used as negative control, and named as MDA-Mock 1 and MDA-Mock 2.

4) Enzyme-Linked Immunosorbent Assay (ELISA)

Antigen levels of PCI and uPA in the media were determined by the enzyme-linked immunosorbent assay (ELISA) using a polyclonal anti-PCI antibody and an anti-uPA antibody, as previously described (Wakita T. et al., Int. J. Cancer 108: 516-23, 2004).

5) RNA Extraction

Total RNA was prepared from MDA-231, MDA-PCI, MDA-R354APCI, MDA-degPCI, and MDA-Mock cells by a modified guanidine thiocyanate-phenol chloroform method, using the RNAzol B reagent (TEL-TEST, Friendswood, Tex.) (Chomczynski P. et al., Anal. Biochem. 162: 156-59, 1987). Total RNA was quantified by spectrometric measurement, and preserved at −80° C., until use.

6) Northern Blot Analysis

Total RNA (20 μg) derived from MDA-231, MDA-PCI, MDA-R354APCI, MDA-degPCI, and MDA-Mock cells were electrophoresed on formaldehyde-agarose gel and transferred onto a GeneScreen nylon membrane (NEN Life Science, Boston, Mass.). After UV-crosslink, the membrane was hybridized with a randomly primed $^{32}$P-labeled full-length human PCI cDNA probe (Suzuki K. et al., J. Biol. Chem. 262: 611-6, 1987).

The membrane was sequentially washed for 20 minutes each with a solution containing 2× sodium chloride-sodium succinate (SSC) [300 mM NaCl, 30 mM sodium succinate, pH7.0] and 0.1% sodium dodecyl sulfate (SDS), then a solution containing 1×SSC and 0.1% SDS, and finally a solution containing 0.1×SSC and 0.1% SDS, exposed on an imaging plate, and visualized by using the BAS-2000 image analyzer (FUJIFILM Corporation, Tokyo, Japan). After being hybridized with the human PCI cDNA probe, the membrane was boiled in 0.5% SDS and hybridized with the $^{32}$P-labeled human glyceraldehyde-3-phosphate dehydrogenase (GAPDH) cDNA probe (Clontech, Palo Alto, Calif.) as described above.

7) Reverse Transcription (RT)-PCR

The scanty expression of human PCI in MDA-231 cells was evaluated by RT-PCR. By using oligo dT primers and the SUPERSCRIPT® First-Strand cDNA Synthesis Kit (Invitrogen Corp., Carlsbad, Calif.), total RNA (5 μg) extracted from MDA231 cells was reverse transcribed following the manufacturer's instructions. The nucleotide sequences of forward and reverse PCR primers used to amplify human PCI are as described below. The primers indicated by SEQ ID NO: 7 and SEQ ID NO: 8 correspond respectively to positions 733 to 752 and 1289 to 1270 of the PCI cDNA.

```
5'-GAGCAAGACTTCTACGTGAC-3'       (SEQ ID NO: 7)
and

5'-CGGTTCACTTTGCCAAGGAA-3'       (SEQ ID NO: 8)
```

The PCR mixture was composed of PCR buffer (100 mM Tris-HCl, 200 mM KCl, pH8.3), 25 mM MgCl$_2$, 200 μM deoxyribonucleoside (dATP, dGTP, dCTP, dTTP) 0.2 μM each of the forward primer and reverse primer, an adequate amount of diethylpyrocarbonate-treated distilled water, and 2.5 units of Taq polymerase (Roche Biochemicals, Basel, Switzerland). Next, a given amount of the mixture was dispensed in the PCR tube containing 2 μl of cDNA sample and amplified using the PC-800 Program Temp Control System (ASTEC, Co., Ltd., Fukuoka, Japan). Subsequently, the PCR product was electrophoresed on 1% agarose gel and stained with 0.5 μg/ml ethidium bromide.

8) Plasmid Construction and Expression of Intact Human PCI, R354APCI, degPCI, Using a Baculoviral Expression System Using the primer pair described below, wild-type PCI cDNA containing no signal peptide sequence was prepared by polymerase chain reaction (PCR) (Saiki R. K. et al., Science 239: 487-91, 1988). The primers indicated by SEQ ID NO: 9 and SEQ ID NO: 10 correspond respectively to positions 133 to 152 and 1296 to 1276 of the PCI cDNA (Hayashi T. et al., Int. J. Hematol. 58: 213-224, 1993). The underlined nucleotides indicate the inserted BamH I site.

```
                                 (SEQ ID NO: 9)
5'-GCGGATCCCCACCGCCACCACCCCCGGGA-3'
and (SEQ ID NO: 10)
5'-GGCGGATCCTCAGGGGCGGTTCACTTTGCC-3'
```

The degPCI cDNA containing no signal peptide sequence was also prepared by PCR using the primer pair described below. The primers indicated by SEQ ID NO: 11 and SEQ ID NO: 12 correspond respectively to positions 133 to 152 and 1194 to 1175 of the PCI cDNA (Hayashi T. et al., Int. J. Hematol. 58: 213-224, 1993). The underlined nucleotides indicate the inserted BamH I site.

```
                                             (SEQ ID NO: 11)
5'-GGCGGATCCCCACCGCCACCACCCCCGGGA-3'
and
                                             (SEQ ID NO: 12)
5'-GGCGGATCCTCACCTGAAAGTGAAGATTGTCC-3'
```

After subcloning the amplified fragments into the BamH I site of pBluescript SKII(+), the DNA sequences of these plasmids were confirmed by the ABI 310 DNA Sequencer (ABI, Foster City, Calif.).

Subsequently, in order to express a fusion protein with the honeybee melittin signal peptide and the immunoglobulin Fc domain, wild-type human PCI cDNA or degPCI cDNA, which contains no signal peptide, was inserted into the baculovirus expression vector pFastBac1-Msp-Fc constructed by using the baculovirus transfer vector pFactBacl (Fujita M. et al., Thromb. Res. 105: 95-102, 2002), pBLUESCRIPT® SKII(+) carrying R354APCI cDNA containing no signal peptide sequence was prepared using the following synthetic oligo nucleotide primers and R354APCI having a signal peptide as a template. The primers indicated by SEQ ID NO: 11 and SEQ ID NO: 14 correspond respectively to positions 133 to 152 and 1296 to 1276 of the PCI cDNA (Hayashi T. et al., Int. J. Hematol. 58: 213-224, 1993). The underlined nucleotides indicate the inserted BamH I site.

```
                                             (SEQ ID NO: 11)
5'-GGCGGATCCCCACCGCCACCACCCCCGGA-3'
and
                                             (SEQ ID NO: 14)
5'-GGCGGATCCTCAGGGGCGGTTCACTTTGCC-3'
```

After confirming the nucleotide sequence of the DNA, appropriate R354APCI cDNA, which does not contain a signal peptide, was inserted into the BamH I site of pFastBac1-Msp-Fc. By using Sf-9 cells cultivated in Grace's insect cell culture medium (Invitrogen Corp., Carlsbad, Calif.) containing 10% FBS, recombinant baculovirus for expressing intact PCI, R354APCI, or degPCI was created and amplified according to the manufacturer's instructions (Invitrogen Corp.). High-Five cells were cultured in the serum-free medium EX-CELL 400 (JRH, BIOSCIENCES, Lenexa, Kans., United States), infected with baculoviruses, and incubated at 27° C. for 72 hours.

9) Purification of Recombinant Intact PCI, R354APCI and degPCI

Culture supernatant of each recombinant PCI (intact PCI, R354APCI and degPCI) was collected, and concentrated by salting out with a final concentration of 70% $(NH_4)_2SO_4$ in the presence of 10 mM benzamidine. After centrifugation, precipitates were recovered, dissolved in 50 mM Tris-HCl containing 10 mM benzamide (pH7.5), and dialyzed against 50 mM Tris-HCl, containing 1 mM benzamide (pH7.5). Next, each dialysis sample was passed through a 0.22 μm filter (MILLEX-HA) and subjected to a 5 ml column of Hitrap CM FF equilibrated with the same buffer but containing no benzamide. After washing the column with the equilibrated buffer, proteins were eluted in a linear gradient of 0 M to 0.5 M NaCl at 720 μl/min, and 1 ml fraction was recovered. Next, a fraction containing PCI was recovered and dialyzed against a Tris-HCl buffer containing 50 mM NaCl, pH7.4 and subjected to a 1 ml column of HiTrap heparin FF equilibrated with the same buffer. Proteins were eluted in a linear gradient of 0.05 M to 0.5 M NaCl at 500 μl/min, and 500 μl fractions were recovered. As described below, each recombinant PCI was detected by Western blot analysis. The fraction containing recombinant PCI was recovered, concentrated and demineralized by VIVASPIN 6 ml CONCENTRATOR (VIVASCIENCE, Hanover, Germany). A given fractionated amount of purified recombinant PCI dissolved in phosphate-buffered saline (PBS) was subjected to sodium dodecyl sulfate-polyacrylamide gel electrophoresis (SDS-PAGE) under reducing condition and then silver stained.

10) SDS Polyacrylamide Electrophoresis (SDS-PAGE) and Western Blot Analysis

SDS-PAGE was performed using the Laemmli method (Laemmli U. K. et al., Nature 227: 680-5, 1970). After electrophoresis, the proteins in the gel were electrically transferred onto a nitrocellulose membrane. Next, intact PCI, R354APCI, and degPCI on the membrane were detected by Western blot analysis as follows. The membrane was treated with anti-PCI rabbit IgG (Non-Patent Document 4), and then treated with anti-rabbit IgG alkaline phosphatase conjugate. Bands on the nitrocellulose membrane were visualized using the Western Blue Stabilized Substrate, as previously described.

11) Assay for Measuring Recombinant PCI Activity

The activity of various recombinant PCIs was determined as follows. 10 μl of APC (40 μg/ml) was mixed with 10 μl of TBS containing 30 U/ml heparin and 10 μl of recombinant intact PCI, R354APCI or degPCI (40 μg/ml). The obtained mixtures were incubated for 20 minutes at 37° C., and then mixed with 250 μl of buffer containing 0.2 mM S-2366, 50 mM Tris-HCl (pH8.0), and 0.1 M CsCl. The obtained mixtures were incubated for 15 minutes at room temperature, and 25 μl of 100% acetic acid was added to stop the reaction. Absorbances at 405 nm were measured by using the Model 550 Microplate Reader (Bio-RAD). Calibration curves were created by using a serial dilution of APC, and residual APC activities were calculated.

12) In Vitro Infiltration Assay

The invasiveness of MDA-231 cells was assayed as disclosed by Albini (Albini A. et al., Cancer Res. 47: 3239-45, 1987). Briefly, a 6.4 mm-diameter Transwell (Becton Dickinson, Mountain View, Calif.), which is equipped with a track-etched polyethylene terephthalate (PET) membrane filter (pore size of 8 μm) coated with 25 μg/filter of Matrigel basement membrane matrix extracted from Engelbreth-Holm-Swarm (EHS) mouse sarcoma, was used. After drying for one night, a cell culture insert containing 8 μm polycarbonate membrane was swollen for two hours at 37° C. in serum-free DMEM. Wild-type, intact PCI, R354APCI, degPCI, or Mock expressing MDA-231 cell line was recovered by trypsinization and washed with DMEM that contains no FBS or proteinase inhibitor.

Next, in the presence or absence of purified PCI, R354APCI, degPCI, and uPA (Technoclone, Vienna, Austria), cells $(2\times10^5)$ were suspended in 500 μl of FBS-free DMEM and put in a culture insert (upper chamber). The lower chamber was filled with 750 μl of DMEM containing 10% FBS used as a chemoattractant. After 24 hours of incubation at 37° C. under 5% $CO_2$, the upper membrane surface of each insert was gently wiped by a cotton swab to remove all non-infiltrating cells and Matrigel. Infiltrating cells on the lower surface of the membrane was fixed and stained using the Diff-Quik Stain Kit (International Reagents Co., Ltd. Kobe, Japan). Cells were counted under a light microscope at 100-fold magnification.

13) Animals

In order to evaluate the metastatic ability and growth of various MDA-231 cells in vivo, male and female severe combined immunodeficient (SCID) mice (five weeks old) were purchased from Clea Japan Inc. (Osaka, Japan). Mice were bred in a constant cycle of 12 hours light/12 hours dark and were allowed to freely access standard food and water. The experiment was approved by the Animal Experiment Ethics Committee of Mie University, and was performed following the National Institute of Health guidelines for experimental animals.

14) Evaluation of Tumor Growth In Vivo

MDA-PCI, MDA-R354APCI, MDA-degPCI, or MDA-Mock cells ($5\times10^5$ cells) in 0.2 ml of sterile DMEM were intradermally injected into the lateral region of a five week old male SCID mouse. Tumor size was measured once a week using calipers, and tumor growth was monitored. Tumor volume was determined according to the following formula: $V=(L\times W^2)\times 0.52$, wherein L is the length and W is the width.

15) Experimental Lung Metastasis Assay

Sub-confluent MDA-PCI, MDA-R354APCI, MDA-degPCI, or MDA-Mock cells were recovered by using EDTA solution, and resuspended to an appropriate density ($2.5\times10^6$ cells/ml) by using serum-free DMEM. Next, MDA-PCI, MDA-R354APCI, MDA-degPCI, or MDA-Mock cells were injected into the caudal vein of a female SCID mouse. Thirty five days after tumor injection, the mouse was anesthetized by pentobarbital and sacrificed. The lungs were excised and fixed in a formaldehyde neutral buffer. Small tumors seen as white patches were counted with a magnifying glass.

16) Matrigel Implant Assay

As previously disclosed (McMahon G. A. et al., J. Biol. Chem. 276: 33964-68, 2001), 0.5 ml of Matrigel (9-10 mg/ml; Becton Dickinson, Franklin Lake, N.J.) containing MDA-PCI, MDA-R354APCI, MDA-degPCI, or MDA-Mock cells ($2\times10^6$ cells/ml), VEGF, and heparin of various concentrations were subcutaneously injected into the center of the abdomen of each male SCID mouse. Three days later, capillary vessels growing toward the Matrigel plug were visualized using a digital camera system (Olympus, Melville, N.Y.). In a parallel experiment, the Matrigel plug was digested by 1 ml of 0.1% collagenase dissolved in Hank's balanced salt solution and the number of new blood vessels was quantified by hemoglobin assay (Passaniti A. et al., Lab. Invest. 67: 519-28, 1992).

17) Chick Chorioallantoic Membrane (CAM) Assay

A square plastic wrap was fixed to an open plastic tube (diameter of 8 cm, backward 6 cm) provided with a ring to prepare an egg hammock. A fertilized egg (three days old) was opened, and the content was transferred to the egg hammock and manipulated such that the embryo came up to the surface of the egg. In order to maintain sterility, the hammock was covered with the lid of a Petri dish. The embryo was maintained in a humidified incubator at 37° C. In a hood, 50 µl of 2% methylcellulose was dried over a Petri dish for one night to prepare a methylcellulose disk. The disk was removed from the dish, placed over the CAM, and intact PCI, R354APCI, or degPCI was applied to the disk. An image of CAM was taken using a digital camera system (Olympus, Melville, N.Y.) and by the NIH Image 1.61 (NIH, Bethesda, Md.). The number of intact blood vessels in random six fields of vision of 100-fold magnification was counted.

18) In Vitro Angiogenesis Assay

As previously disclosed (Schnaper H. W. et al., J. Cell Physiol. 165: 107-18, 1995), capillary vessel formation assay on the Matrigel was performed. A 24-well plate was coated with Matrigel (Becton Dickinson, Franklin Lake, N.J.) at 4° C., and polymerized for 30 minutes at 37° C. HUVEC was inoculated ($2\times10^4$ cells/well) on the Matrigel-coated plate. In the absence of heparin, cells were incubated together with intact PCI, R354APCI, or degPCI (10 µg/ml), or without these PCIs (control). Six hours after incubation, capillary vessel formation was visually evaluated under a phase-contrast microscope. The number of intact blood vessels in random six fields of vision of 100-fold magnification was counted.

19) Statistical Analysis

Values were all represented as average values±standard deviation of average values. Each experiment was repeated at least three times. Significant difference was evaluated by variance analysis. The value for which $P<0.05$ was regarded as statistically significant.

Results

Example 1

Figure 2:
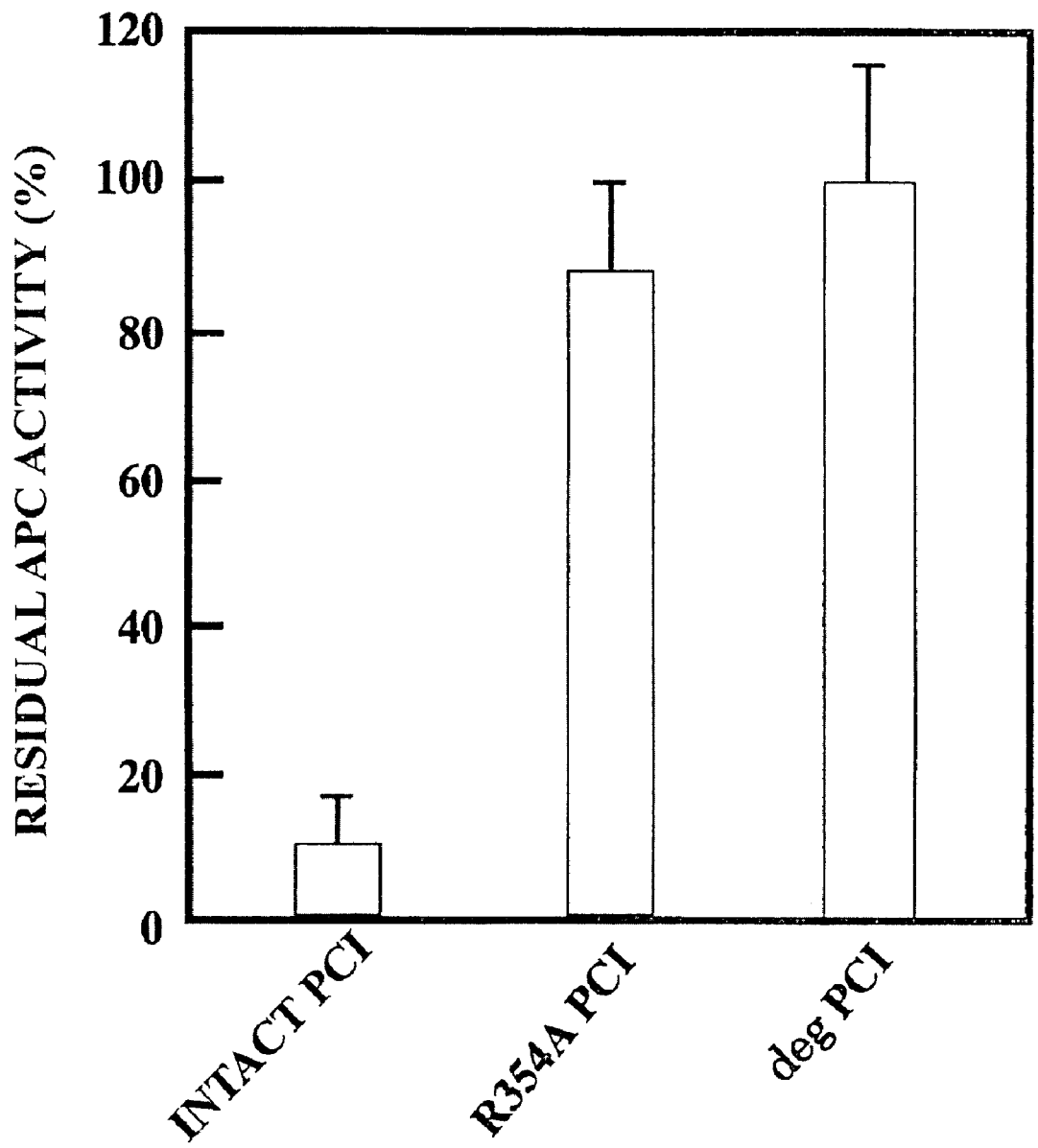
FIG. 2 presents a graph showing APC inhibition by recombinant intact PCI, R354APCI, and degPCI. The inhibitory activity of each recombinant PCI against human APC was determined as follows. In the presence of heparin (10 U/ml), each recombinant protein (40 μg/ml) was incubated with human APC (40 μg/ml) for 20 minutes. Then, residual APC activity was determined using S-2366.

Expression, Purification and APC Inhibitory Activity of Recombinant Intact PCI, R354APCI, and degPCI Produced by the Baculovirus Expression System Intact PCI, R354APCI, and degPCI expressed by the baculovirus expression system were purified by using Hitrap CM FF and Hitrap heparin FF. Next, purified proteins were detected by Western blot analysis under reducing condition. MW of intact PCI, R354APCI, and degPCI were about 57 KDa, about 57 KDa, and about 54 KDa, respectively (FIG. 1). The APC inhibitory activity of these recombinant PCIs were also examined. R354APCI and degPCI could hardly inhibit APC (FIG. 2).

Example 2

Figure 3A:
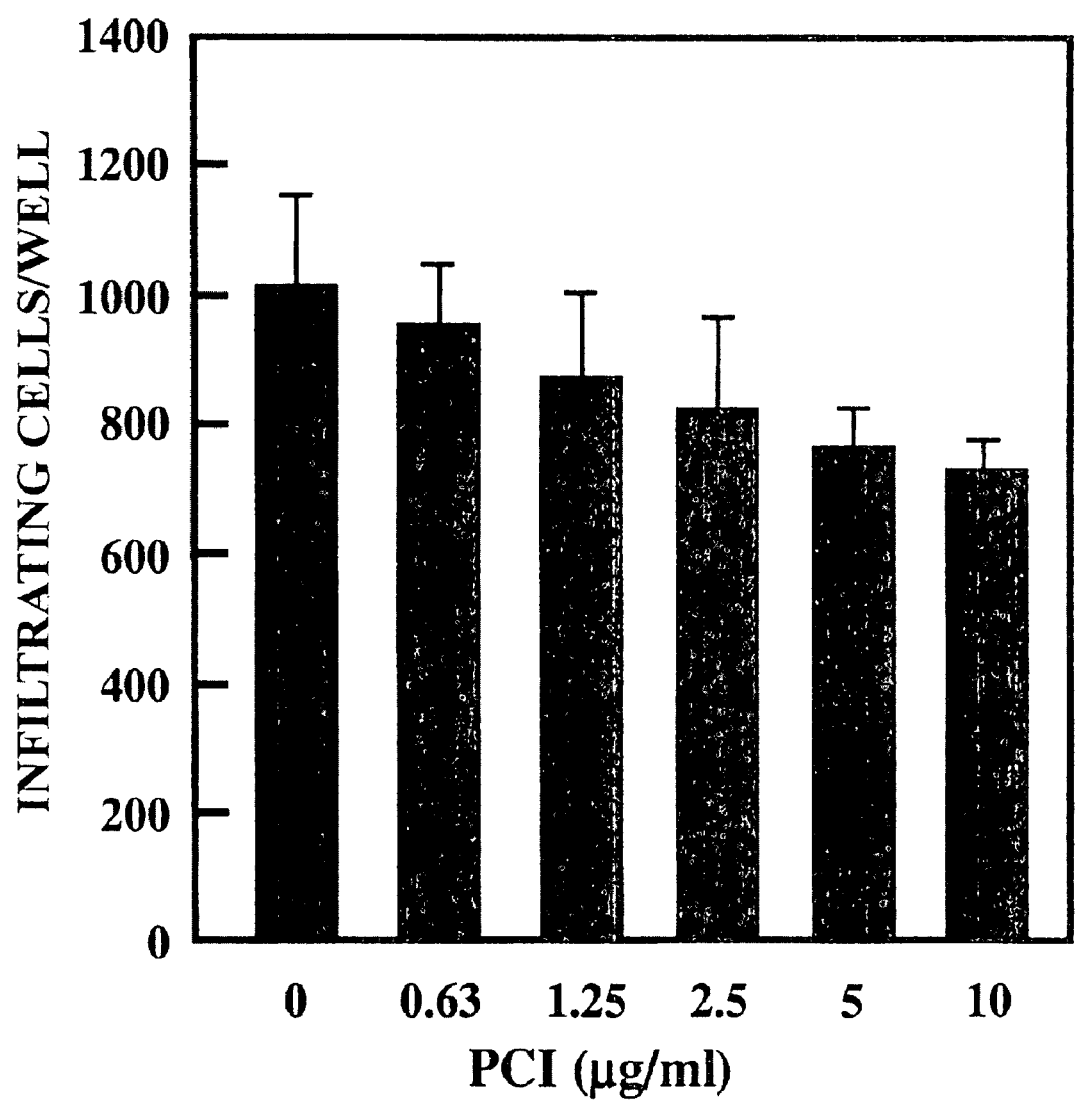
FIG. 3A presents a graph showing the effect of PCI on the infiltration activity of untransfected MDA-231 cells.
Figure 3B:
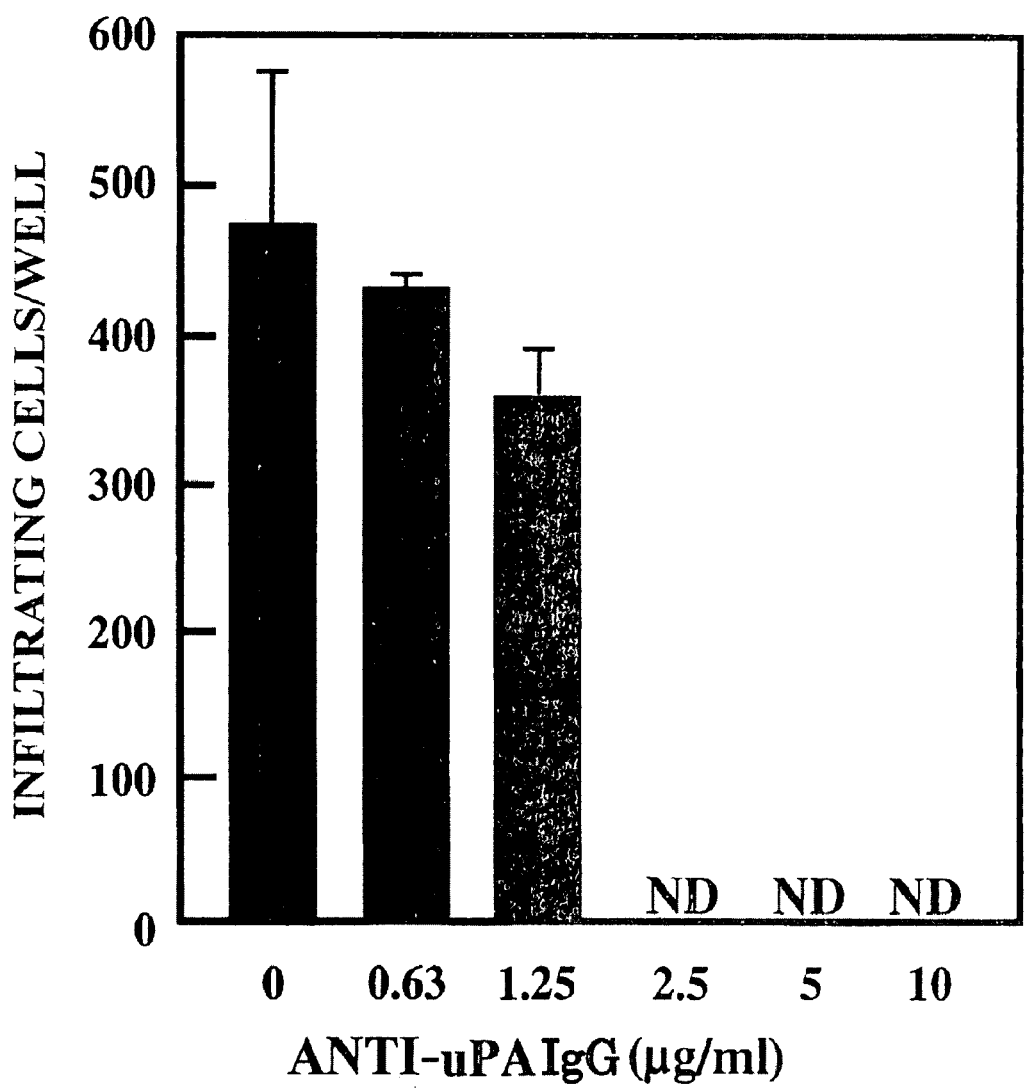
Figure 3C:
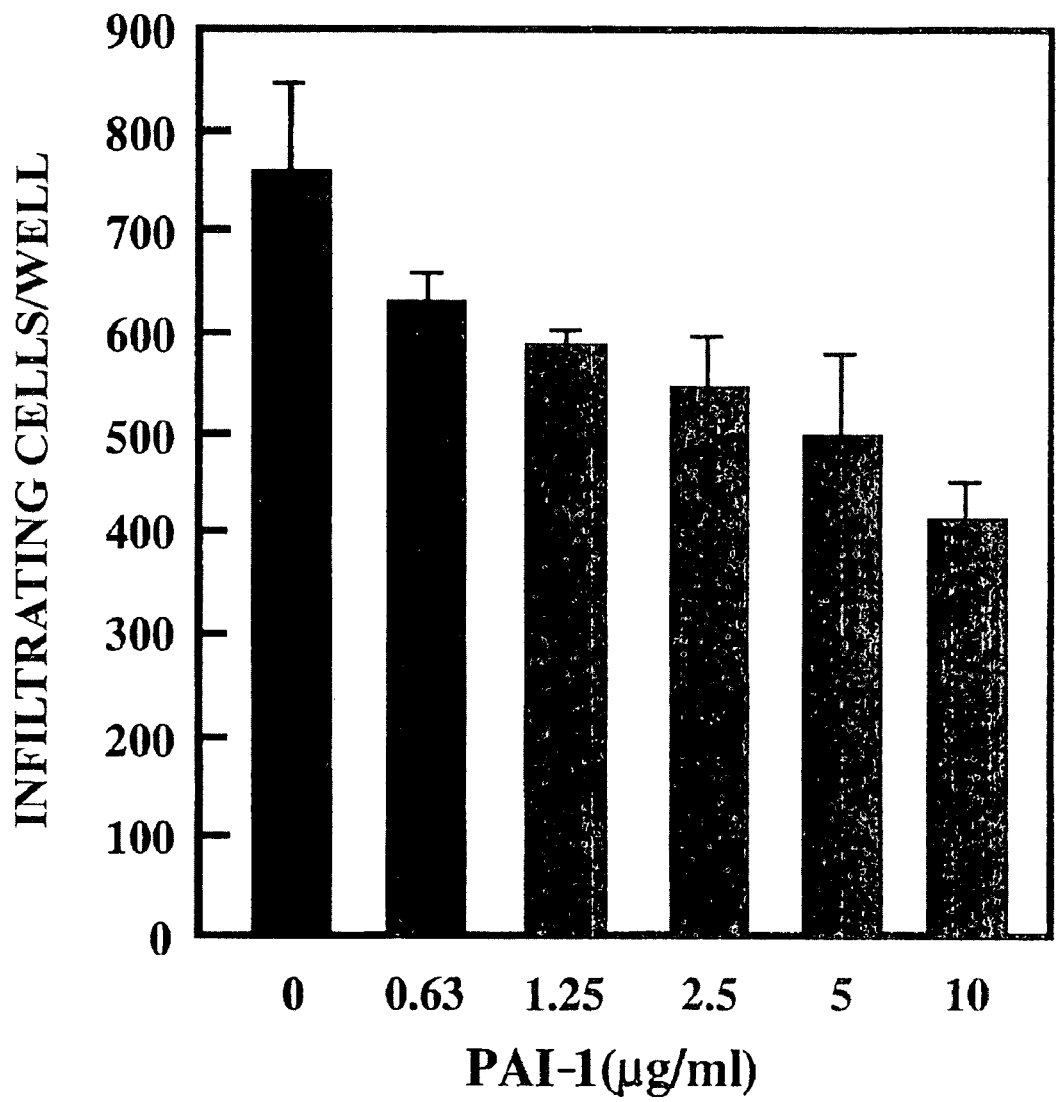
Figure 3D:
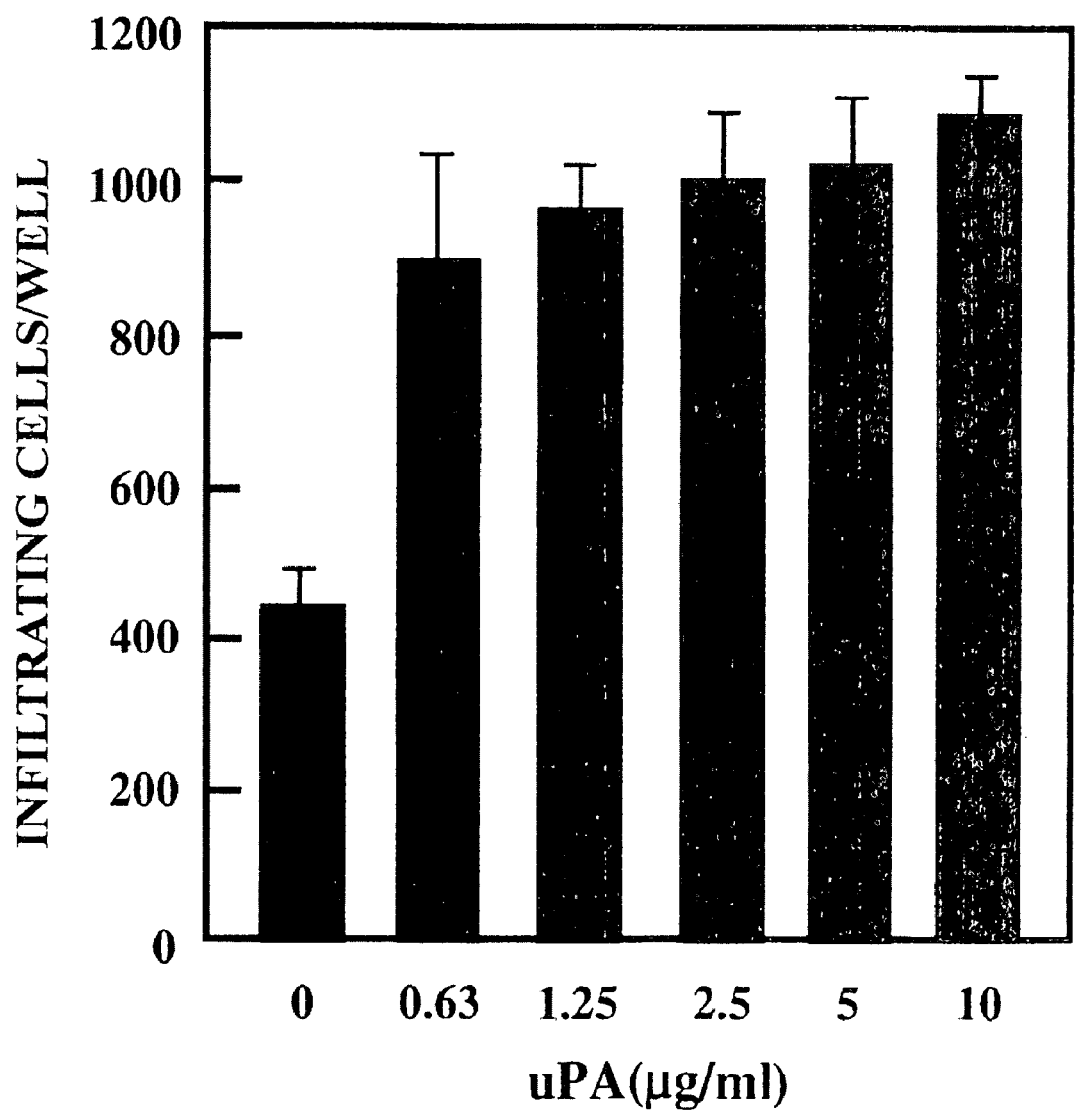

Effects of PCI, Anti-Human uPA Antibody, PAI-1, and uPA on the Invasiveness of MDA-231 Cells Effects of intact PCI on the invasiveness of MDA-231 cells in the Matrigel system are examined. First, uPA and PCI expressions in MDA-231 cells were evaluated by ELISA and RT-PCR analysis. The MDA-231 cells express uPA of 470 ng/$10^4$ cells/24 hours and PCI of 58 ng/$10^4$ cells/24 hours. RT-PCR analysis also indicated that MDA-231 cells express both uPA mRNA and PCI mRNA (data not shown). Subsequently, the effect of PCI on the infiltration activity of MDA-231 cells was examined. Intact PCI significantly inhibited the infiltration activity of MDA-231 cells in a dose-dependent manner (FIG. 3A); however, BSA did not have an effect on this activity (data not shown). Further, the anti-human PCI antibody dose-dependently inhibited PCI-induced inhibition of MDA-231 cell infiltration (data not shown). Infiltration assay also showed that the invasiveness of MDA-231 cells was inhibited by the anti-uPA antibody (FIG. 3B) and PAI-1 (FIG. 3C), and dose-dependently promoted by uPA (FIG. 3D).

Example 3

Figure 4:
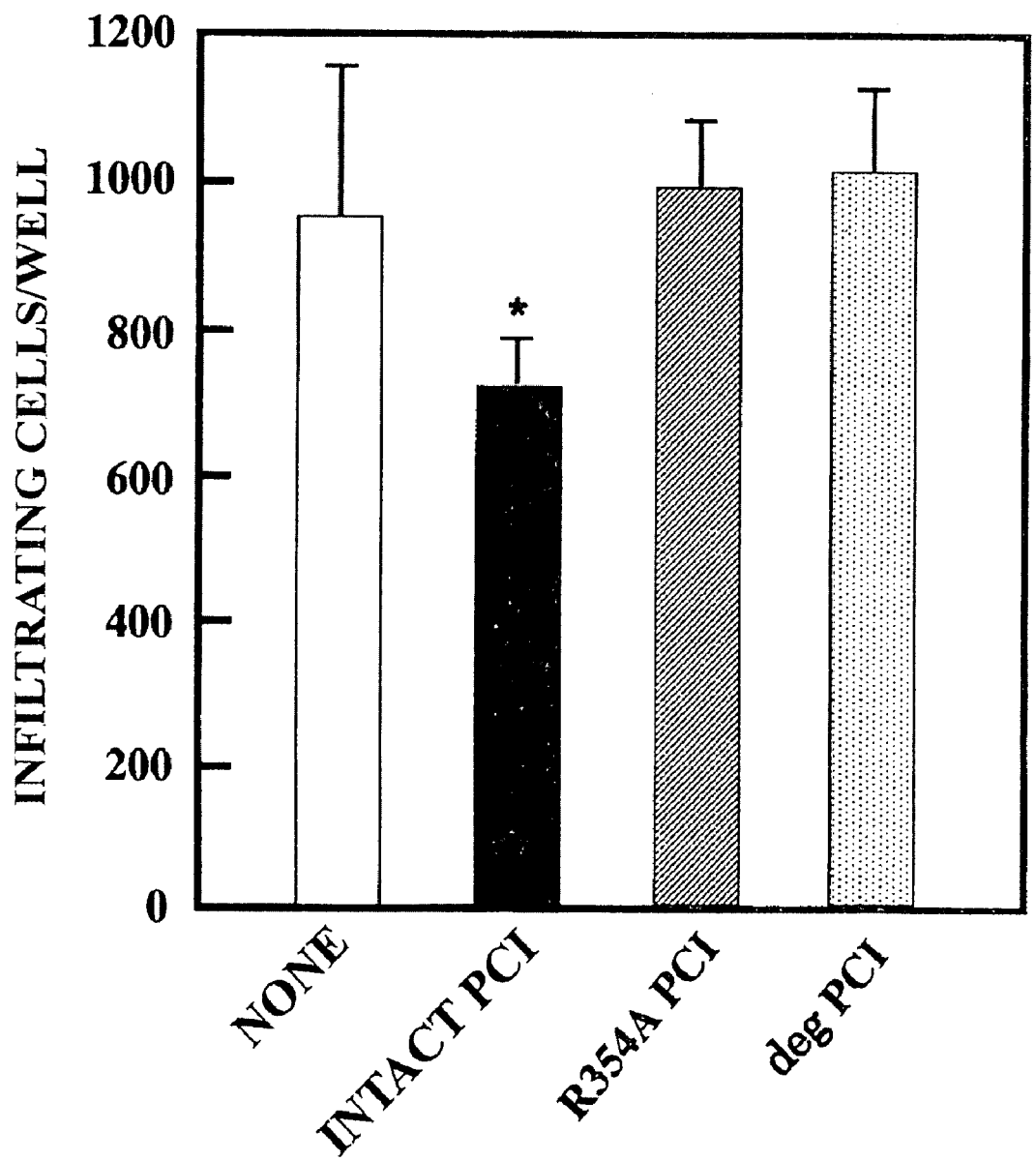
FIG. 4 presents a graph showing the effects of recombinant intact PCI, R354APCI, and degPCI on the infiltration of MDA-231 cells. Untransfected MDA-231 cells ($2\times10^5$) were suspended in 500 μl DMEM in the presence of 10 μg/ml intact PCI, R354APCI, or degPCI, and placed into a culture insert (upper chamber). The lower chamber contained 750 μl of 10% FBS-DMEM as a chemoattractant. After 24 hours of incubation, infiltrating cells on the lower surface of the membrane were fixed and stained. The cells were counted under the light microscope at 100-fold magnification. Data are shown as the number of cells (mean±S.D.) derived from four independent infiltration membranes. *p<0.05.

Effects of Intact PCI, R354APCI, and degPCI on the Invasiveness of MDA-231 Cells In order to evaluate whether the inhibitory activity of PCI on the invasiveness of MDA-231 cells depends on the protease inhibitory activity of PCI or not, the effects of intact PCI, R354APCI, and degPCI on the invasiveness of MDA-231 cells were evaluated. As shown in FIG. 4, although intact PCI significantly inhibited the invasiveness of MDA-231 cells, neither R354APCI nor degPCI inhibited the infiltration of MDA-231 cells. These findings suggest that the protease inhibitory activity of PCI is necessary for inhibiting the invasiveness of MDA-231 cells in vitro.

Example 4

Expression of Intact PCI, R354APCI, or degPCI in MDA-231 Cells Transfected with an Expression Vector for Each PCI In order to evaluate whether the expression of intact PCI, R354APCI, and degPCI affects the invasiveness, growth, and metastatic ability of MDA-231 cells, two PCI-expressing MDA-231 cell lines (MDA-PCI 1, MDA-PCI 2); two mutant PCI-expressing MDA-231 cell lines (MDA-R354APCI 1, MDA-R354APCI 2); two degPCI-expressing MDA-231 cell lines (MDA-degPCI 1, MDA-degPCI 2); and two Mock transfection cell lines (MDA-Mock 1, MDA-Mock 2) were prepared. MDA-PCI, MDA-R354APCI, and MDA-degPCI cell lines showed strong expression of each PCI mRNA; on the other hand, untransfected MDA cells and MDA-Mock cell lines expressed intact PCI weakly (data not shown). The amounts of PCI secreted by MDA-PCI 1 and MDA-PCI 2 cells were 10.3 ng/$10^4$ cells/24 hours and 12.5 ng/$10^4$ cells/24 hours, respectively. The amounts of R354APCI secreted by MDA-R354APCI 1 and MDA-R354APCI 2 cells were 20.0 ng/$10^4$ cells/24 hours and 12.0 ng/$10^4$ cells/24 hour, respectively. The amounts of degrading-type PCI secreted by MDA-degPCI 1 and MDA-degPCI 2 cells were 3.0 ng/$10^4$ cells/24 hours and 1.1 ng/$10^4$ cells/24 hours, respectively. Growth rate and uPA production in these cell lines were nearly identical (data not shown).

Example 5

Figure 5:
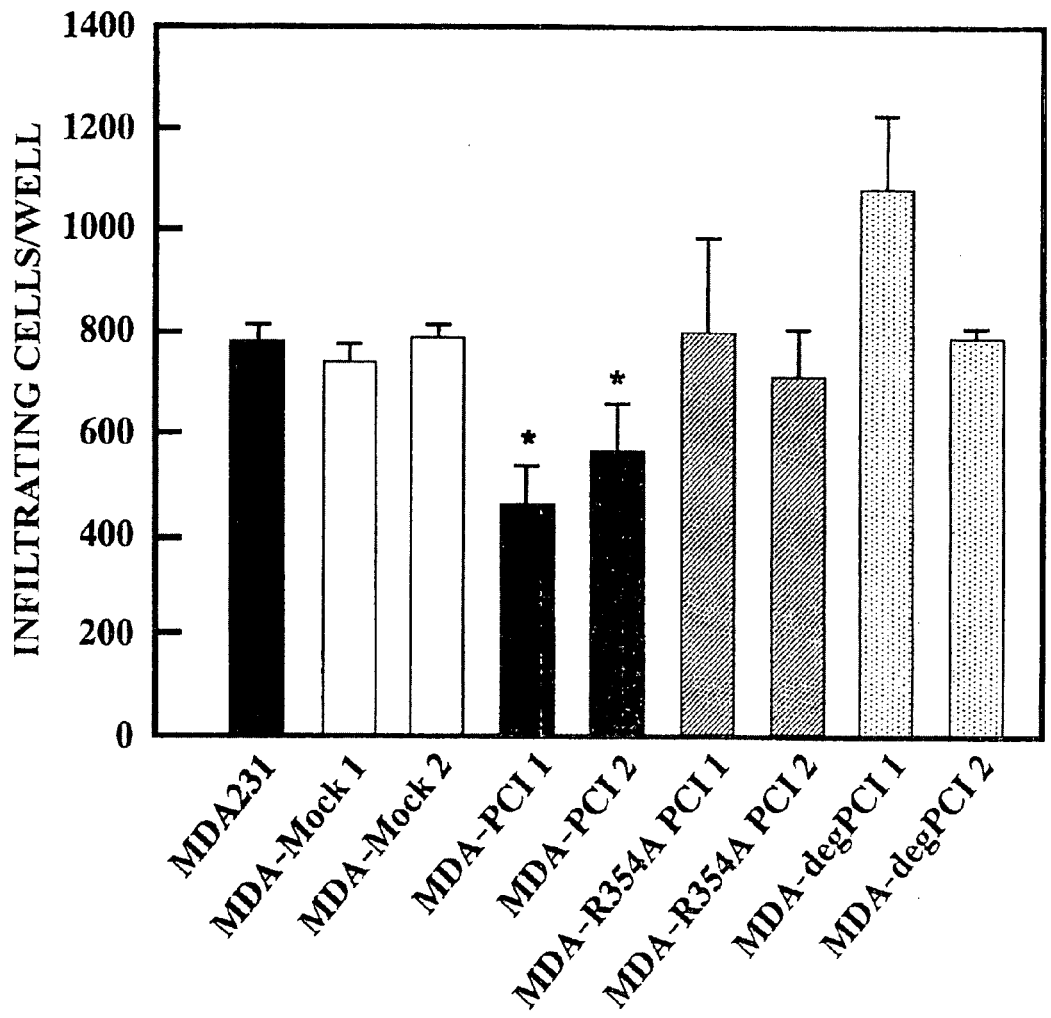
FIG. 5 presents a graph showing the infiltration activity of MDA-231 cells expressing intact PCI, R354APCI, or degPCI. MDA-PCI, MDA-R354APCI, MDA-degPCI, or MDA-Mock cells ($2\times10^5$) were suspended in 500 μl DMEM and placed into a culture insert (upper chamber). The subsequent experiment procedure was essentially the same as that in the description of FIG. 4. Data are shown as the number of cells (mean±S.D.) derived from four independent infiltration membranes. *p<0.05.

Effects of Intact PCI, R354APCI, or degPCI Expression on the Invasiveness of MDA-231 Cells In Vitro In order to determine whether the expression of intact PCI, R354APCI, or degPCI affects the invasion ability of MDA-231 cells, the invasiveness of PCI, R354APCI, degPCI expressing MDA-231 cells and Mock transfection MDA-231 cells in Matrigel was evaluated in vitro. As shown in FIG. 5, the invasiveness of two MDA-PCI cell lines was significantly lower than that of the MDA-Mock cell line. The invasiveness of MDA-R354APCI and MDA-degPCI was not significantly different from that of the MDA-Mock cell line. From these findings, it is suggested that PCI expressed in MDA-231 cells inhibits infiltration and that the inhibitory activity of PCI against the infiltration of MDA-231 cells depends on its protease inhibitory activity. These data are consistent with the effects of recombinant R354APCI and degPCI on the invasiveness of the above-described MDA-231 cells.

Example 6

Effects of Intact PCI, R354APCI, or degPCI on the Growth of MDA-231 Cells

Figure 6:
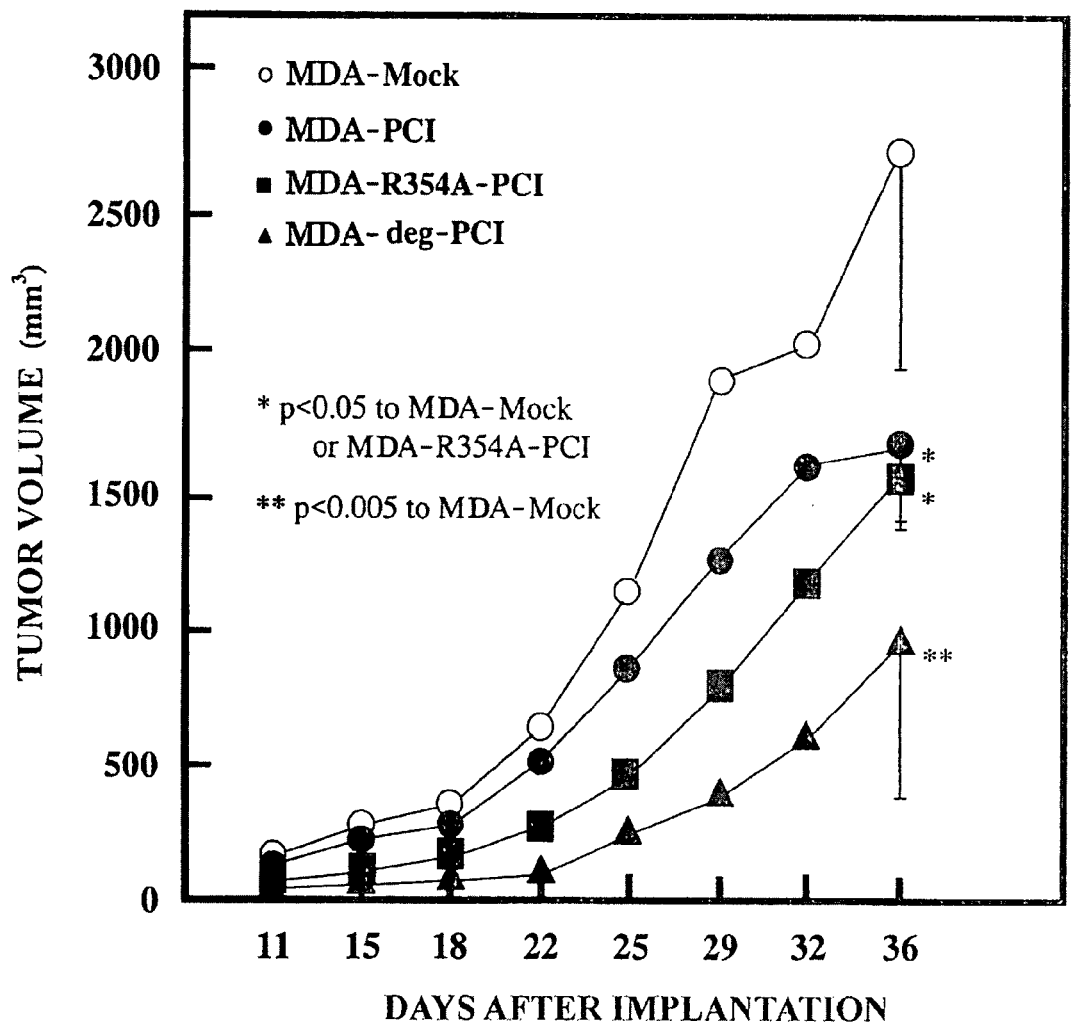
FIG. 6 presents a graph showing the growth of the intact PCI, R354APCI, and degPCI-expressing MDA-231 cells in SCID mice. $2 \times 10^5$ cells of MDA-PCI, MDA-R354APCI, MDA-degPCI, or MDA-Mock in 200 μl sterilized DMEM were intradermally injected into the abdominal wall of a five-week-old male SCID mouse. Tumor volume was measured by calipation.

In order to evaluate the effect of PCI on tumor growth in vivo, the growth of Mock, PCI-, R354APCI-, or degPCI-expressing MDA-231 cells implanted into the dorsal side of a mouse was monitored. As shown in FIG. 6, the growth of the MDA-PCI cell line was significantly lower than that of the Mock cell line. Surprisingly, the growth of MDA-R354APCI and MDA-degPCI also was significantly lower than that of the MDA-Mock cell line, and was the same as or a little lower than the growth of MDA-PCI. From these findings, it is suggested that PCI inhibits tumor growth in vivo, and that the growth inhibitory activity of PCI does not depend on its protease inhibitory activity.

Example 7

Figure 7:
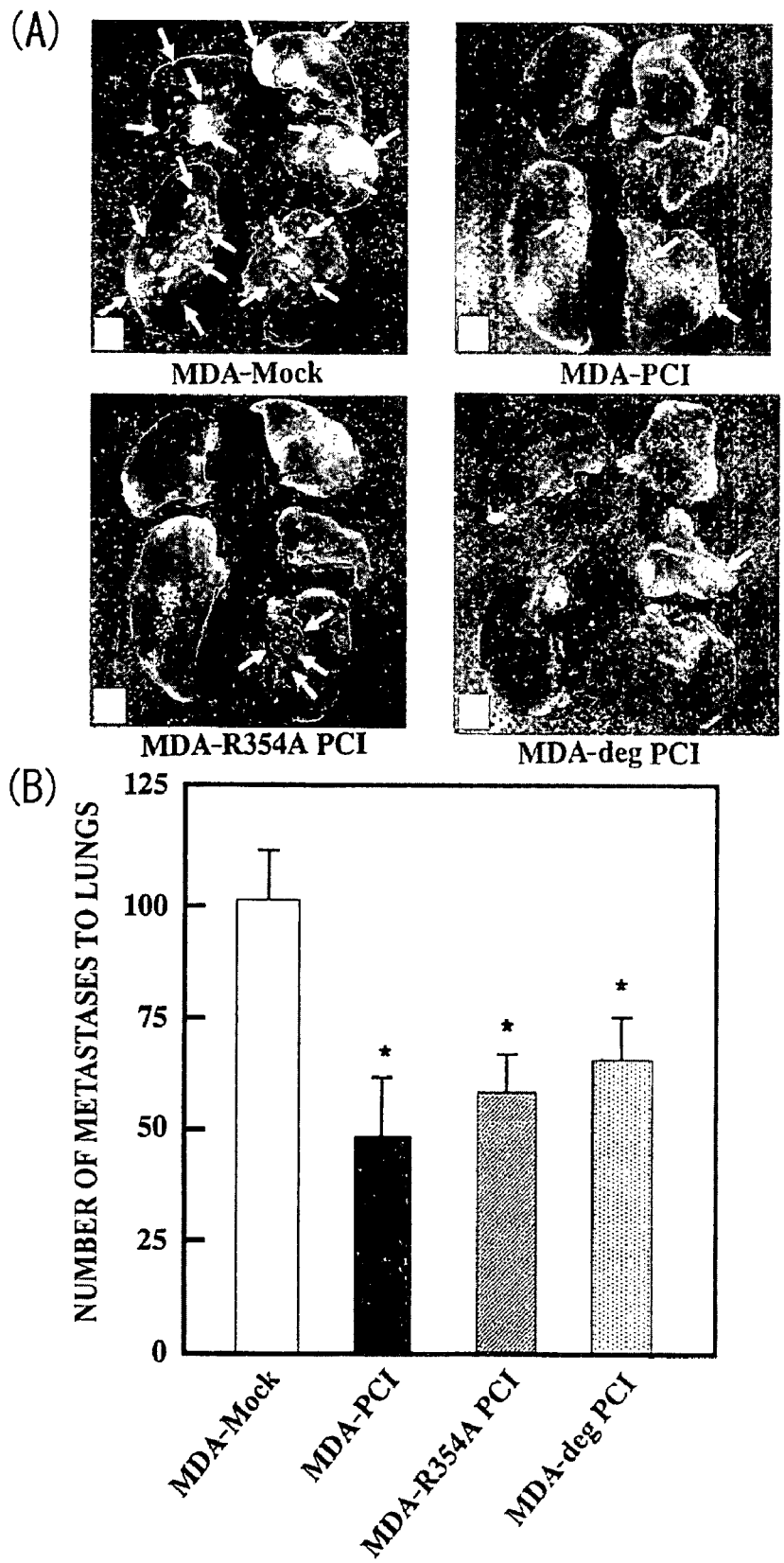
FIG. 7 presents a graph and photographs showing experimental metastases of intact PCI, R354APCI, and degPCI-expressing MDA-231 cells in SCID mice. MDA-PCI, MDA-R354APCI, MDA-degPCI, or MDA-Mock cells ($2 \times 10^5$) were suspended in 200 μl DMEM and intravenously injected into a five-week-old female SCID mouse. Lungs were isolated and fixed after 35 days, and metastasis formation in the lungs was quantified by counting tumor sites. Photograph (A) shows representative results, and graph (B) shows the number of growing sites (mean±S.D.) in six mice.

Effects of Intact PCI, R354APCI, or degPCI on the Metastatic Ability of MDA-231 Cells The effect of PCI on the metastatic ability of MDA-231 cells was tested by injecting MDA-Mock, MDA-PCI, MDA-R354APCI, or MDA-degPCI via the caudal vein, and then counting the number of metastatic small tumors in the lung. As shown in FIGS. 7A and 7B, the number of small lung tumors for the MDA-PCI, MDA-R354APCI, or MDA-degPCI cell lines was significantly lower than that of the MDA-Mock cell line. Further, the metastatic small tumors of the MDA-R354APCI and MDA-degPCI cell lines were slightly larger than those of the MDA-PCI cell line. These data demonstrate that PCI inhibits tumor metastasis in vivo, and that the inhibitory activity of PCI on tumor metastasis does not depend on its protease inhibitory activity.

Example 8

Effects of Intact PCI, R354APCI, or degPCI on In Vivo Angiogenesis

Figure 8:
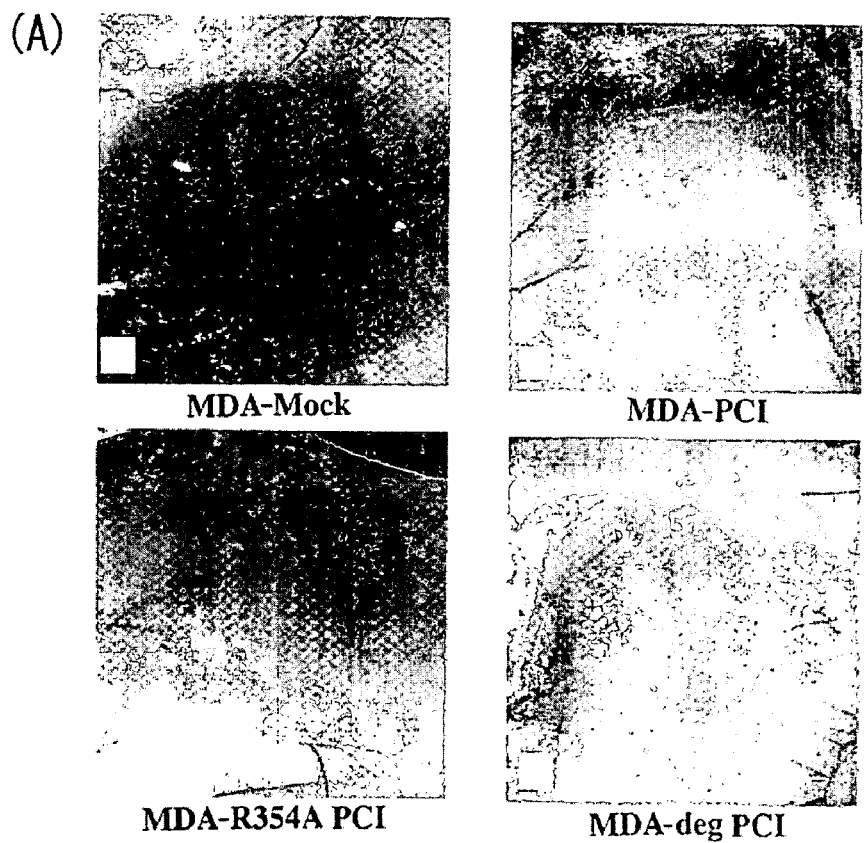
FIG. 8 presents a graph and photographs showing the quantitative analysis of neovascularization and angiogenesis in SCID mice using Matrigel containing intact PCI, R354APCI, or degPCI-expressing MDA-231 cells. 0.5 ml of Matrigel containing MDA-PCI, MDA-R354APCI, MDA-degPCI, or MDA-Mock ($2 \times 10^6$ cells), as well as VEGF and various concentrations of heparin, was subcutaneously injected near the middle of the abdomen of each male SCID mouse. Three days later, neovascularization toward the Matrigel was photographed by the digital camera system (Olympus, Melville, N.Y.) (A). Simultaneously, Matrigel plugs were removed and digested by 1 ml of 0.1% collagenase dissolved in Hank's solution, and neovascularization was quantified by hemoglobin assay. Individual n>6 and mean±S.D. are shown in (B).
Figure 8:
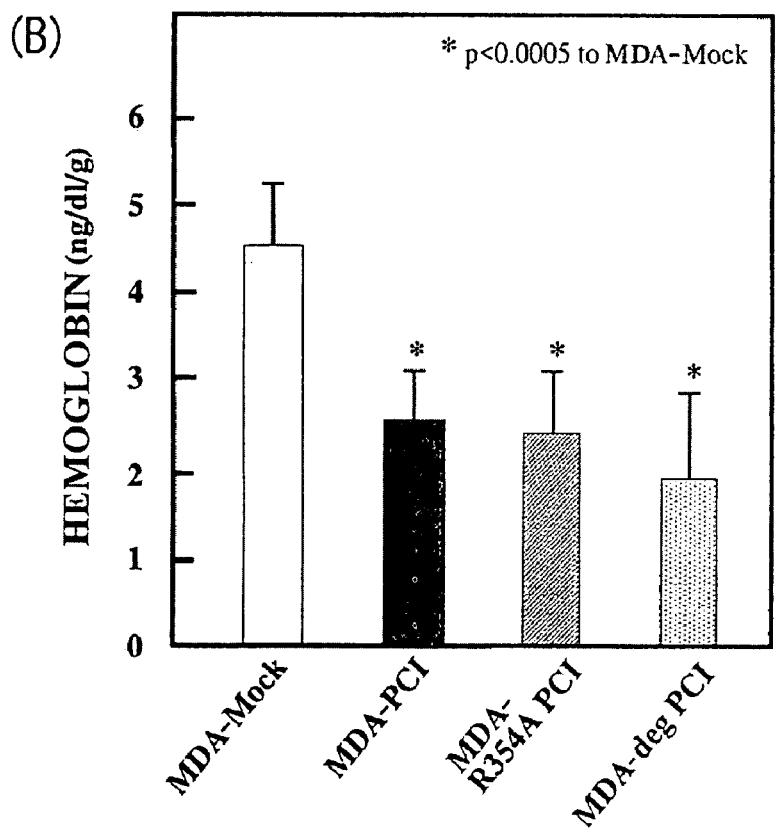
Figure 9:
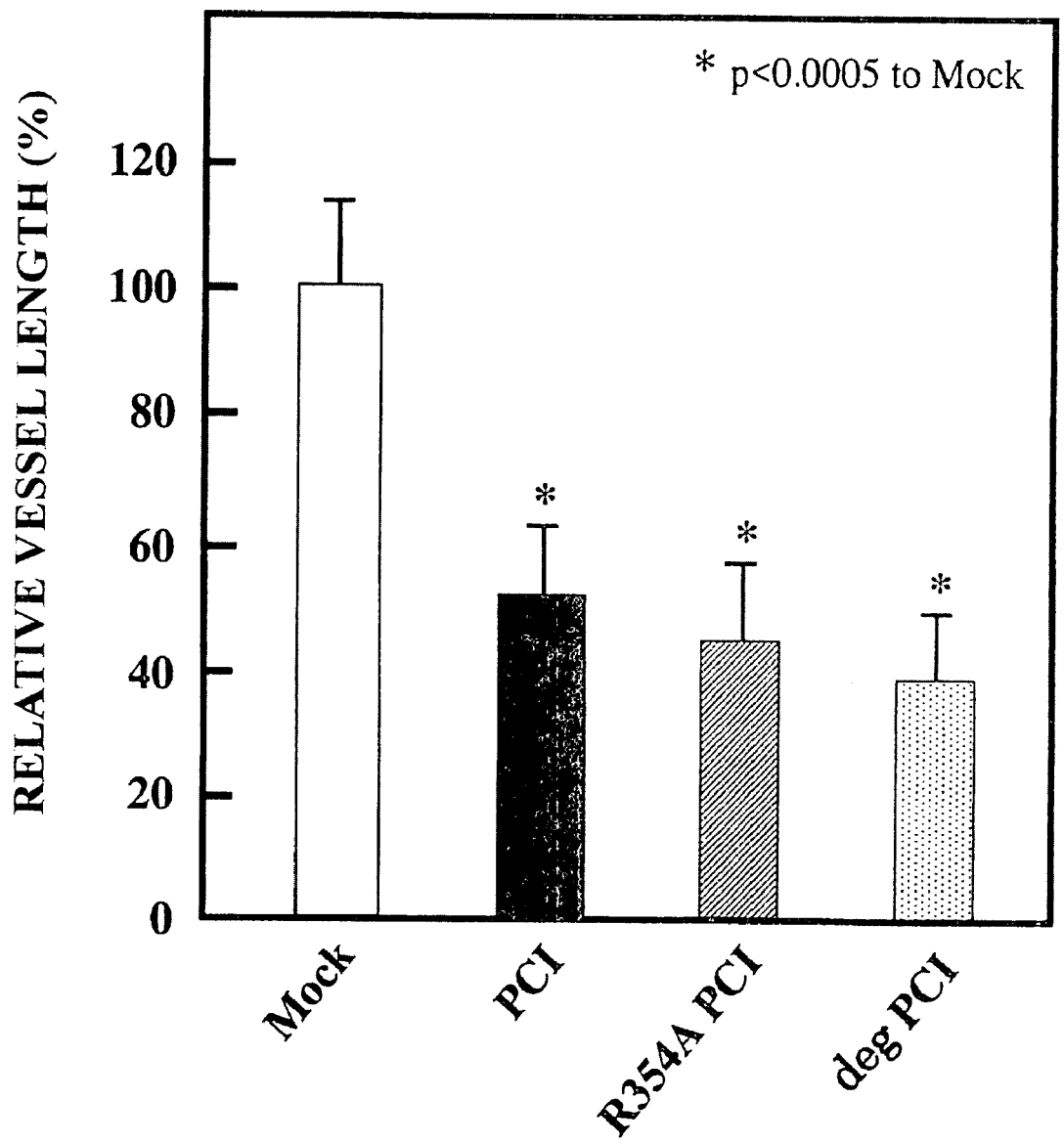
FIG. 9 presents a graph showing the effects of intact PCI, R354APCI, and degPCI on angiogenesis in the chorioallantoic membrane (CAM). A disk containing intact PCI, R354APCI, or degPCI was applied to an embryo CAM. An image of CAM was taken using the digital camera system (Olympus, Melville, N.Y.) and NIH image 1.61 (NIH, Bethesda, Md.). The length of neovessels was measured in pixels. The results are presented as means±S.D. *p<0.05.

The effect of PCI on VEGF-induced angiogenesis was tested by using animals subcutaneously injected with Matrigel containing VEGF, heparin, and intact PCI-, R354APCI-, degPCI-expressing, or Mock MDA-231 cells. FIG. 8A shows that angiogenesis in the Matrigel containing PCI-expressing MDA-231 cells, R354APCI-expressing MDA-231 cells or degPCI-expressing MDA-231 cells was lower than that of the Mock MDA-231 cells. As shown in FIG. 8B, the hemoglobin level in the Matrigel containing MDA-PCI cells, MDA-R354APCI cells, or MDA-degPCI cells was significantly lower than that of Matrigel containing the MDA-Mock cells. Subsequently, the anti-angiogenic activity of various recombinant PCIs was demonstrated by chick CAM assay in vivo. As shown in FIG. 9, PCI significantly inhibited vessel growth in the chick CAM assay. The PCI-treated CAM was significantly smaller than the control, and there was little angiogenesis. R354APCI and degPCI also significantly inhibited vessel growth. These data show that the PCI inhibits angiogenesis in vivo and that the inhibitory activity does not depend on its protease inhibitory activity. This result is consistent with the observation described in the in vivo assay.

Example 9

Effects of Intact PCI, R354APCI or degPCI on the HUVEC Tube Formation

Figure 10:
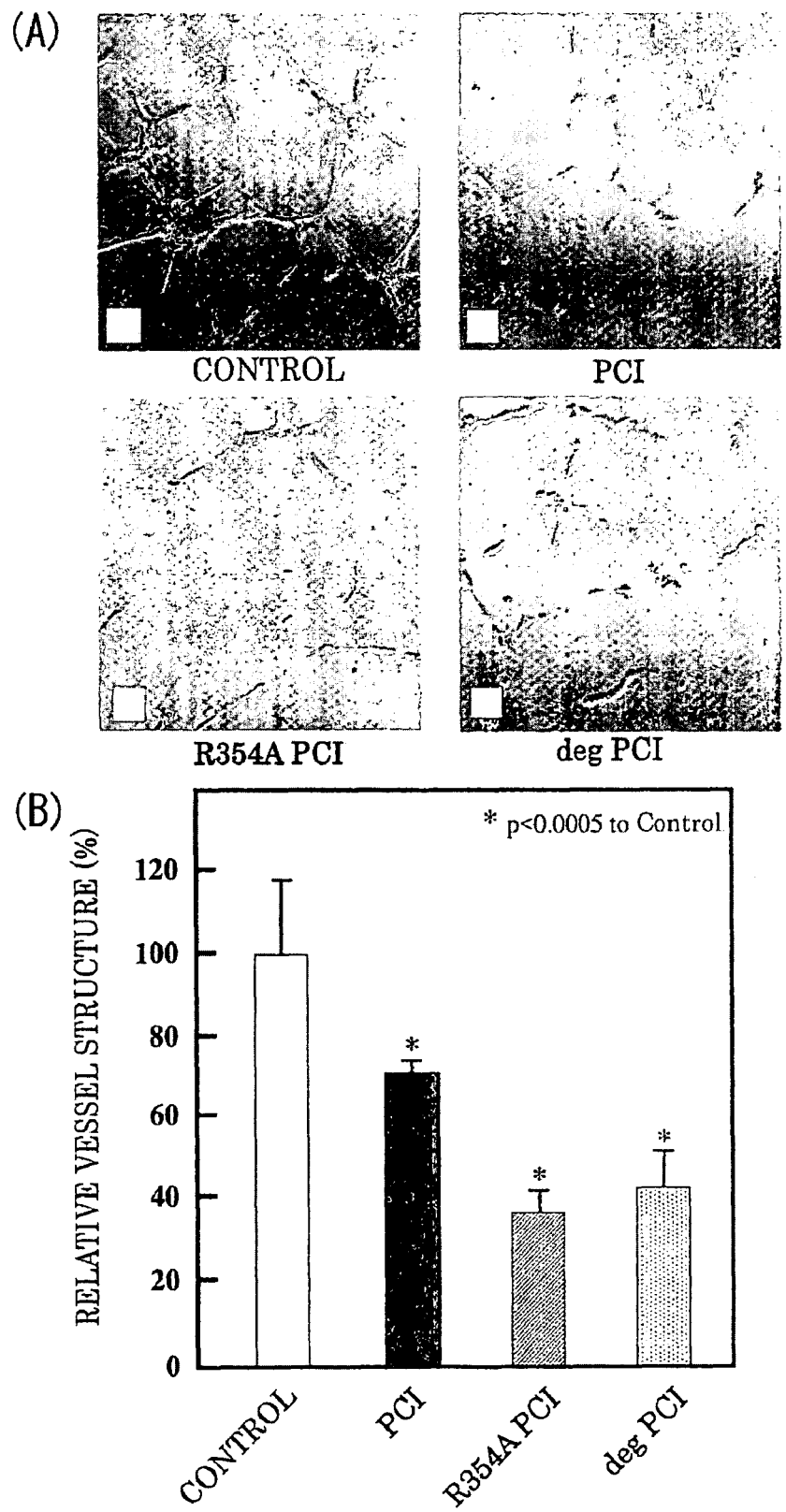
FIG. 10 presents a graph and photographs showing the effects of intact PCI, R354APCI, and degPCI on the tube formation of HUVEC. On 24-well plates coated with Matrigel, HUVEC cells ($2 \times 10^4$ cells) were cultured in MCDB-131 supplemented with 5% FBS in the presence of 10 μg of intact PCI, R354APCI or degPCI, or in the absence of these PCIs (control). Six hours after the plating, photographs were taken (at 100-fold magnification) (A), and the effects of various PCI recombinant variants on tube formation were quantitatively analyzed (B). The tube length was measured in pixels, and results are presented as means±S.D. *p<0.05.

Various effects of PCI on HUVEC angiogenesis were evaluated in vitro. As shown in FIGS. 10A and 10B, tube formation was inhibited by intact PCI, R354APCI and degPCI. Further, the anti-human PCI antibody dose-dependently inhibited the PCI-induced inhibition of tube formation (data not shown). Interestingly, the angiogenesis inhibitory activities of R354APCI and degPCI were significantly stronger than that of intact PCI. These data may explain why the subcutaneously implanted R354APCI or degPCI expressing MDA-231 cells grow more slowly than the intact PCI expressing MDA-231 cells.

<Discussion>

Recently, the present inventors have demonstrated that the expression of PCI is significantly decreased in kidney cancer cells as compared with nonneoplastic kidney tissues, and that the expression of PCI inhibits the infiltration activity of Caki-1 kidney cancer cells (Wakita T. et al., Int. J. Cancer 108: 516-23, 2004). Furthermore, the effects of PCI on tumor growth and metastasis were evaluated in vivo by using PCI-expressing Caki-1 cells; however, even wild-type Caki-1 cells could not grow in SCID mice. Based on this fact, the effect of PCI on the invasiveness of MDA-231 breast cancer cells was tested. MDA-231 cells expressed a large amount of uPA and a small amount of PCI.

Although purified PCI effectively and significantly inhibited the infiltration activity of MDA-231 cells, the inhibitory activity of PCI was weaker than that for the infiltration of Caki cells. This result can probably be attributed to the uPA expression in MDA-231, which is greatly higher than in Caki-1 cells. Further, the infiltration activity of MDA-231 cells was increased by uPA addition and inhibited by PAI-1. The result is consistent with the idea that the infiltration of MDA-231 is mediated mainly by uPA. Furthermore, the present inventors evaluated the effect of PCI on the infiltration activity of B16 mouse melanomas cells and discovered a similar result (data not shown). From these findings, PCI is suggested to control infiltration of various types of tumor cells.

Furthermore, the present inventors prepared a number of recombinant mutant PCIs to evaluate their inhibitory activities on the infiltration of MDA-231 cells, and found that intact PCI inhibits the infiltration activity of MDA-231 cells. N terminal fragments of R354APCI (reactive site mutant) and protease degrading type PCI do not have inhibitory activity against APC. From this, it is suggested that the inhibitory activity of PCI against the in vitro tumor cell infiltration depends on its protease inhibitory activity.

Subsequently, the present inventors found that PCI-expressing MDA-231 cells are less invasive than the Mock-transfected MDA-231 cells. This finding is consistent with previous data showing that PCI-expressing Caki-1 cells are less invasive than Mock-transfected Caki-1 cells. The present inventors tested the effect of PCI protease inhibitory activity on the infiltration ability of MDA-231 cells, and demonstrated that the infiltration abilities of the degPCI-expressing MDA-231 cells and R354APCI-expressing MDA-231 cells were not significantly different from that of the Mock MDA-231 cells. This result is consistent with the data showing that recombinant R354APCI and degPCI do not affect the infiltration of MDA-231 cells in vitro.

Next, by using various PCI-expressing MDA-231 cells, the in vivo effects of PCI on the growth and metastasis of MDA-231 cells in SCID mice were tested. Data showed that PCI inhibited both the tumor growth and metastasis in vivo. Surprisingly, R354APCI and degPCI also demonstrated strong inhibitory activity against tumor growth and metastasis. This suggests that the inhibitory activity of PCI on tumor growth and metastasis is not mediated by its protease inhibitory activity.

Kallistatin is a heparin-binding serpin that inhibits tumor growth through suppression of angiogenesis (Miao R. Q. et al., Blood 100: 3245-52, 2002). It is well known that VEGF and bFGF are strong mediators of angiogenesis and that the binding of VEGF and bFGF to heparan sulfate proteoglycan at the endothelial cell surface controls the binding of VEGF and bFGF to specific receptors (Folkman J. et al., Adv. Exp. Med. Biol. 313: 355-64, 1992). It has also been reported that heparin itself promotes VEGF-dependent angiogenesis (Folkman J. et al., Adv. Exp. Med. Biol. 313:355-64, 1992).

Kallistatin inhibits angiogenesis by its heparin-binding ability, and this binding is important for VEGF to bind to its receptor, and therefore VEGF-mediated angiogenesis is inhibited by Kallistatin (Miao R. Q. et al., Am. J. Physiol. Cell Physiol. 284: C1604-13, 2003). Latent type antithorombin (AT), which is a heparin-binding serpin, is also known to have antiangiogenic activity (O'Reilly M. S. et al., Science 285: 1926-8, 1999). It has been recently reported that the latent-type AT down-regulates the expression of perlecan, which is a proangiogenic proteoglycan, in endothelial cells (Zhang W. et al, Blood 103: 1185-91, 2004). PCI also is a heparin-binding serpin like Kallistatin and AT. In the present invention, the present inventors discovered that PCI inhibits the growth and metastasis of MDA-231, and evaluated the effect of PCI on angiogenesis.

First, the effect of intact PCI-expressing MDA-231 cells incorporated in Matrigel on VEGF-induced angiogenesis in the presence of heparin was evaluated. VEGF-induced angiogenesis was inhibited in Matrigel containing the intact PCI-expressing MDA-231 cells; however, it was not inhibited in Matrigel containing the Mock MDA-231 cells. Further, the inhibitory activity against angiogenesis induced by VEGF in the presence of heparin was also recognized in Matrigel containing R354APCI-expressing MDA-231 cells or MDA-231 cells that express the N-terminal fragment of degrading type PCI. The antiangiogenic activity of intact PCI, R354APCI, and degPCI was confirmed by the CAM assay and the tube formation in endothelial cells. These data suggest that the PCI inhibition of angiogenesis is not mediated by its protease inhibitory activity. These findings are consistent with the inhibitory activity of the intact PCI, R354APCI, and degPCI against tumor growth and metastasis observed in the in vivo experiments. It has been reported recently that APC promotes angiogenesis through its protease activity (Uchiba M. et al., Circ. Res. 95: 34-41, 2004). However, in the present invention, PCI did not inhibit the activity of APC to suppress angiogenesis.

Next, the effect of heparin on the angiogenesis inhibitory activity of intact PCI-expressing MDA-231 cells was evaluated. Angiogenesis in Matrigel containing PCI-expressing cells almost completely disappeared in the presence of a large amount of heparin (data not shown). Further, angiogenesis inhibitory activity was also recognized in Matrigel containing R354APCI- and degPCI-expressing MDA-231 cells. These findings suggest that PCI acts as a competitor of VEGF for heparin, and that PCI inhibits angiogenesis by binding to heparin or heparin-like glycosaminoglycan at the endothelial cell surface. This data is consistent with the previous report indicating that the N-terminal domain of the truncated form of AT which lacks inhibitory activity but has the heparin-binding activity has antiangiogenic activity (O'Reilly M. S. et al., Science 285: 1926-8, 1999), and that kallistatin with a mutation in its heparin-binding site does not have antiangiogenic activity (Miao R Q et al., Blood 100: 3245-52, 2002). It has been reported that the heparin-binding site of PCI is located on the H and D helix of the serpin molecule that contains positively charged residues (Neese L. L. et al., Arch. Biochem. Biophys. 355: 101-8, 1998) (Shirk R. A. et al., J. Biol. Chem. 269: 28690-5, 1994).

In summary, the present inventors proved that PCI inhibits tumor growth and metastasis in vivo, and that the anti-metastasis and anti-growth activities of PCI do not depend on its protease inhibitory activity. These findings suggest that PCI is potentially useful in the treatment of various tumors such as renal cell carcinoma, breast cancer, and the like.

INDUSTRIAL APPLICABILITY

The present invention revealed that PCI inhibits cancer infiltration in a protease inhibitory action-dependent manner. Therefore, PCI derivatives having protease inhibitory action is useful as an inhibitor of cancer infiltration. On the other hand, PCI's angiogenesis inhibitory activity in cancer does not depend on its protease inhibitory action. Similarly, it was shown that PCI's cancer cell growth inhibitory activity does not depend on its protease inhibitory activity. Therefore, PCI derivatives that have low or deleted protease inhibitory activity are useful as angiogenesis inhibitors and cancer cell growth inhibitors.

Angiogenesis and cell growth are important mechanisms in the malignant transformation of cancer. Therefore, anticancer agents that act against these mechanisms to inhibit the same are useful in preventing malignant cancer transformation and treating malignant cancer. In particular, PCI derivatives that do not have protease inhibitory activity are expected to reduce side effects caused by the protease inhibitory action of PCI.

The invention claimed is:

1. A method for treating cancer in a subject, the method comprising administering to the subject a derivative of a protein C inhibitor, wherein the derivative of the protein C inhibitor comprises an amino acid sequence with at least 90% sequence identity to the mature peptide of SEQ ID NO:2 (residues labeled 1-387 in SEQ ID NO:2) and has a lower protease inhibitory activity than a protein C inhibitor consisting of the mature peptide of SEQ ID NO:2, thereby treating cancer in the subject.

2. The method of claim 1, wherein the derivative of the protein C inhibitor comprises amino acids 1-354 of SEQ ID NO:2.

3. The method of claim 1, wherein the derivative of the protein C inhibitor comprises the amino acid sequence of the mature peptide of SEQ ID NO:2 in which the arginine residue at position 354 is mutated.

4. The method of claim 1, wherein the derivative of the protein C inhibitor consists of amino acids 1-354 of SEQ ID NO:2.

5. A method for treating breast cancer in a subject, the method comprising administering to the subject a protein C inhibitor or derivative thereof, wherein the protein C inhibitor or derivative thereof comprises an amino acid sequence with at least 90% sequence identity to the mature peptide of SEQ ID NO:2 and has protease inhibitory activity, thereby treating breast cancer in the subject.

6. The method of claim 1, wherein the derivative of the protein C inhibitor comprises an amino acid sequence with at least 95% sequence identity to the mature peptide of SEQ ID NO:2.

7. The method of claim 5, wherein the protein C inhibitor or derivative thereof comprises an amino acid sequence with at least 95% sequence identity to the mature peptide of SEQ ID NO:2.

* * * * *

```
                          SEQUENCE LISTING

<160> NUMBER OF SEQ ID NOS: 15

<210> SEQ ID NO 1
<211> LENGTH: 1237
<212> TYPE: DNA
<213> ORGANISM: Homo sapiens
<220> FEATURE:
<221> NAME/KEY: CDS
<222> LOCATION: (11)..(1228)

<400> SEQUENCE: 1
gaattccacc atg cag ctc ttc ctc ctc ttg tgc ctg gtg ctt ctc agc            49
           Met Gln Leu Phe Leu Leu Leu Cys Leu Val Leu Leu Ser
               1               5                   10 cct cag ggg gcc tcc ctt cac cgc cac cac ccc cgg gag atg aag aag           97
Pro Gln Gly Ala Ser Leu His Arg His His Pro Arg Glu Met Lys Lys
    15                  20                  25 aga gtc gag gac ctc cat gta ggt gcc acg gtg gcc ccc agc agc aga          145
Arg Val Glu Asp Leu His Val Gly Ala Thr Val Ala Pro Ser Ser Arg
30                  35                  40                  45 agg gac ttt acc ttc gac ctc tac agg gtc ttg gct tcc gct gcc ccc          193
Arg Asp Phe Thr Phe Asp Leu Tyr Arg Val Leu Ala Ser Ala Ala Pro
                50                  55                  60 agc cag aat atc ttc ttc tcc cct gtg agc atc tcc atg agc ctg gcc          241
Ser Gln Asn Ile Phe Phe Ser Pro Val Ser Ile Ser Met Ser Leu Ala
            65                  70                  75 atg ctc tcc ctg ggg gct ggg tcc agc aca aag atg cag atc ctg gag          289
Met Leu Ser Leu Gly Ala Gly Ser Ser Thr Lys Met Gln Ile Leu Glu
        80                  85                  90 ggc ctg ggc ctc aac ctc cag aaa agc tca gag gag gag ctg cac aga          337
Gly Leu Gly Leu Asn Leu Gln Lys Ser Ser Glu Glu Glu Leu His Arg
    95                  100                 105 ggc ttt cag cag ctc ctt cag gaa ctc aac cag ccc aga gat ggc ttc          385
Gly Phe Gln Gln Leu Leu Gln Glu Leu Asn Gln Pro Arg Asp Gly Phe
110                 115                 120                 125 cag ctg agc ctg ggc aat gcc ctt ttc acc gac ctg gtg gta gac ctg          433
Gln Leu Ser Leu Gly Asn Ala Leu Phe Thr Asp Leu Val Val Asp Leu
                130                 135                 140 cag gac acc ttc gta agt gcc atg aag acg ctg tac ctg gca gac act          481
Gln Asp Thr Phe Val Ser Ala Met Lys Thr Leu Tyr Leu Ala Asp Thr
            145                 150                 155 ttc ccc acc aac ttt agg gac tct gca ggg gcc atg aag cag atc aat          529
Phe Pro Thr Asn Phe Arg Asp Ser Ala Gly Ala Met Lys Gln Ile Asn
        160                 165                 170 gat tat gtg gca aag caa acg aag ggc aag att gtg gac ttg ctt aag          577
Asp Tyr Val Ala Lys Gln Thr Lys Gly Lys Ile Val Asp Leu Leu Lys
    175                 180                 185
```

```
aac ctc gat agc aat gcg gtc gtg atc atg gtg aat tac atc ttc ttt      625
Asn Leu Asp Ser Asn Ala Val Val Ile Met Val Asn Tyr Ile Phe Phe
190             195                 200                 205 aaa gct aag tgg gag aca agc ttc aac cac aaa ggc acc caa gag caa      673
Lys Ala Lys Trp Glu Thr Ser Phe Asn His Lys Gly Thr Gln Glu Gln
        210                 215                 220 gac ttc tac gtg acc tcg gag act gtg gtg cgg gta ccc atg atg agc      721
Asp Phe Tyr Val Thr Ser Glu Thr Val Val Arg Val Pro Met Met Ser
                225                 230                 235 cgc gag gat cag tat cac tac ctc ctg gac cgg aac ctc tcc tgc agg      769
Arg Glu Asp Gln Tyr His Tyr Leu Leu Asp Arg Asn Leu Ser Cys Arg
            240                 245                 250 gtg gtg ggg gtc ccc tac caa ggc aat gcc acg gct ttg ttc att ctc      817
Val Val Gly Val Pro Tyr Gln Gly Asn Ala Thr Ala Leu Phe Ile Leu
                255                 260                 265 ccc agt gag gga aag atg cag cag gtg gag aat gga ctg agt gag aaa      865
Pro Ser Glu Gly Lys Met Gln Gln Val Glu Asn Gly Leu Ser Glu Lys
270                 275                 280                 285 acg ctg agg aag tgg ctt aag atg ttc aaa aag agg cag ctc gag ctt      913
Thr Leu Arg Lys Trp Leu Lys Met Phe Lys Lys Arg Gln Leu Glu Leu
        290                 295                 300 tac ctt ccc aaa ttc tcc att gag ggc tcc tat cag ctg gag aaa gtc      961
Tyr Leu Pro Lys Phe Ser Ile Glu Gly Ser Tyr Gln Leu Glu Lys Val
                305                 310                 315 ctc ccc agt ctg ggg atc agt aac gtc ttc acc tcc cat gct gat ctg     1009
Leu Pro Ser Leu Gly Ile Ser Asn Val Phe Thr Ser His Ala Asp Leu
            320                 325                 330 tcc ggc atc agc aac cac tca aat atc cag gtg tct gag atg gtg cac     1057
Ser Gly Ile Ser Asn His Ser Asn Ile Gln Val Ser Glu Met Val His
                335                 340                 345 aaa gct gtg gtg gag gtg gac gag tcg gga acc aga gca gcg gca gcc     1105
Lys Ala Val Val Glu Val Asp Glu Ser Gly Thr Arg Ala Ala Ala Ala
350                 355                 360                 365 acg ggg aca ata ttc act ttc agg tcg gcc cgc ctg aac tct cag agg     1153
Thr Gly Thr Ile Phe Thr Phe Arg Ser Ala Arg Leu Asn Ser Gln Arg
        370                 375                 380 cta gtg ttc aac agg ccc ttt ctg atg ttc att gtg gat aac aac atc     1201
Leu Val Phe Asn Arg Pro Phe Leu Met Phe Ile Val Asp Asn Asn Ile
                385                 390                 395 ctc ttc ctt ggc aaa gtg aac cgc ccc tgaggatcc                       1237
Leu Phe Leu Gly Lys Val Asn Arg Pro
            400                 405

<210> SEQ ID NO 2
<211> LENGTH: 406
<212> TYPE: PRT
<213> ORGANISM: Homo sapiens
<220> FEATURE:
<221> NAME/KEY: SIGNAL
<222> LOCATION: (1)..(19)
<220> FEATURE:
<221> NAME/KEY: mat_peptide
<222> LOCATION: (20)..(406)

<400> SEQUENCE: 2

Met Gln Leu Phe Leu Leu Leu Cys Leu Val Leu Leu Ser Pro Gln Gly
                -15                 -10                 -5

Ala Ser Leu His Arg His His Pro Arg Glu Met Lys Lys Arg Val Glu
        -1   1                   5                  10

Asp Leu His Val Gly Ala Thr Val Ala Pro Ser Ser Arg Arg Asp Phe
        15                  20                  25

Thr Phe Asp Leu Tyr Arg Val Leu Ala Ser Ala Ala Pro Ser Gln Asn
```

```
                30                  35                  40                  45
        Ile Phe Phe Ser Pro Val Ser Ile Ser Met Ser Leu Ala Met Leu Ser
                            50                  55                  60

Leu Gly Ala Gly Ser Ser Thr Lys Met Gln Ile Leu Glu Gly Leu Gly
                        65                  70                  75

Leu Asn Leu Gln Lys Ser Ser Glu Glu Leu His Arg Gly Phe Gln
                    80                  85                  90

Gln Leu Leu Gln Glu Leu Asn Gln Pro Arg Asp Gly Phe Gln Leu Ser
                95                  100                 105

Leu Gly Asn Ala Leu Phe Thr Asp Leu Val Val Asp Leu Gln Asp Thr
        110                 115                 120                 125

Phe Val Ser Ala Met Lys Thr Leu Tyr Leu Ala Asp Thr Phe Pro Thr
                        130                 135                 140

Asn Phe Arg Asp Ser Ala Gly Ala Met Lys Gln Ile Asn Asp Tyr Val
                    145                 150                 155

Ala Lys Gln Thr Lys Gly Lys Ile Val Asp Leu Leu Lys Asn Leu Asp
                    160                 165                 170

Ser Asn Ala Val Val Ile Met Val Asn Tyr Ile Phe Phe Lys Ala Lys
        175                 180                 185

Trp Glu Thr Ser Phe Asn His Lys Gly Thr Gln Glu Gln Asp Phe Tyr
        190                 195                 200                 205

Val Thr Ser Glu Thr Val Val Arg Val Pro Met Met Ser Arg Glu Asp
                        210                 215                 220

Gln Tyr His Tyr Leu Leu Asp Arg Asn Leu Ser Cys Arg Val Val Gly
                    225                 230                 235

Val Pro Tyr Gln Gly Asn Ala Thr Ala Leu Phe Ile Leu Pro Ser Glu
                    240                 245                 250

Gly Lys Met Gln Gln Val Glu Asn Gly Leu Ser Glu Lys Thr Leu Arg
        255                 260                 265

Lys Trp Leu Lys Met Phe Lys Lys Arg Gln Leu Glu Leu Tyr Leu Pro
        270                 275                 280                 285

Lys Phe Ser Ile Glu Gly Ser Tyr Gln Leu Glu Lys Val Leu Pro Ser
                        290                 295                 300

Leu Gly Ile Ser Asn Val Phe Thr Ser His Ala Asp Leu Ser Gly Ile
                    305                 310                 315

Ser Asn His Ser Asn Ile Gln Val Ser Glu Met Val His Lys Ala Val
                    320                 325                 330

Val Glu Val Asp Glu Ser Gly Thr Arg Ala Ala Ala Thr Gly Thr
        335                 340                 345

Ile Phe Thr Phe Arg Ser Ala Arg Leu Asn Ser Gln Arg Leu Val Phe
        350                 355                 360                 365

Asn Arg Pro Phe Leu Met Phe Ile Val Asp Asn Asn Ile Leu Phe Leu
                        370                 375                 380

Gly Lys Val Asn Arg Pro
                    385

<210> SEQ ID NO 3
<211> LENGTH: 21
<212> TYPE: DNA
<213> ORGANISM: Artificial Sequence
<220> FEATURE:
<223> OTHER INFORMATION: an artificially synthesized primer sequence

<400> SEQUENCE: 3
ttcactttcg cgtcggcccg c                                                   21
```

```
<210> SEQ ID NO 4
<211> LENGTH: 21
<212> TYPE: DNA
<213> ORGANISM: Artificial Sequence
<220> FEATURE:
<223> OTHER INFORMATION: an artificially synthesized primer sequence

<400> SEQUENCE: 4
gcgggccgac gcgaaagtga a                                             21

<210> SEQ ID NO 5
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 5
gcgaattcct ctggcagagc ctccgtttcc                                    30

<210> SEQ ID NO 6
<211> LENGTH: 31
<212> TYPE: DNA
<213> ORGANISM: Artificial Sequence
<220> FEATURE:
<223> OTHER INFORMATION: an artificially synthesized primer sequence

<400> SEQUENCE: 6
gcgaattctc acctgaaagt gaagattgtc c                                  31

<210> SEQ ID NO 7
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 7
gagcaagact tctacgtgac                                               20

<210> SEQ ID NO 8
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 8
cggttcactt tgccaaggaa                                               20

<210> SEQ ID NO 9
<211> LENGTH: 29
<212> TYPE: DNA
<213> ORGANISM: Artificial Sequence
<220> FEATURE:
<223> OTHER INFORMATION: an artificially synthesized primer sequence

<400> SEQUENCE: 9
gcggatcccc accgccacca cccccggga                                     29

<210> SEQ ID NO 10
<211> LENGTH: 30
<212> TYPE: DNA
<213> ORGANISM: Artificial Sequence
<220> FEATURE:
<223> OTHER INFORMATION: an artificially synthesized primer sequence
```

-continued

```
<400> SEQUENCE: 10
ggcggatcct caggggcggt tcactttgcc                                       30

<210> SEQ ID NO 11
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 11
ggcggatccc caccgccacc accccgggA                                        30

<210> SEQ ID NO 12
<211> LENGTH: 32
<212> TYPE: DNA
<213> ORGANISM: Artificial Sequence
<220> FEATURE:
<223> OTHER INFORMATION: an artificially synthesized primer sequence

<400> SEQUENCE: 12
ggcggatcct cacctgaaag tgaagattgt cc                                    32

<210> SEQ ID NO 13
<211> LENGTH: 31
<212> TYPE: DNA
<213> ORGANISM: Artificial Sequence
<220> FEATURE:
<223> OTHER INFORMATION: an artificially synthesized primer sequence

<400> SEQUENCE: 13
ggcggatccc caccgccacc acccccggg a                                      31

<210> SEQ ID NO 14
<211> LENGTH: 30
<212> TYPE: DNA
<213> ORGANISM: Artificial Sequence
<220> FEATURE:
<223> OTHER INFORMATION: an artificially synthesized primer sequence

<400> SEQUENCE: 14
ggcggatcct caggggcggt tcactttgcc                                       30

<210> SEQ ID NO 15
<211> LENGTH: 354
<212> TYPE: PRT
<213> ORGANISM: Homo sapiens

<400> SEQUENCE: 15
```

His Arg His His Pro Arg Glu Met Lys Lys Arg Val Glu Asp Leu His
1               5                   10                  15

Val Gly Ala Thr Val Ala Pro Ser Ser Arg Arg Asp Phe Thr Phe Asp
                20                  25                  30

Leu Tyr Arg Val Leu Ala Ser Ala Ala Pro Ser Gln Asn Ile Phe Phe
            35                  40                  45

Ser Pro Val Ser Ile Ser Met Ser Leu Ala Met Leu Ser Leu Gly Ala
        50                  55                  60

Gly Ser Ser Thr Lys Met Gln Ile Leu Glu Gly Leu Gly Leu Asn Leu
65                  70                  75                  80

Gln Lys Ser Ser Glu Glu Glu Leu His Arg Gly Phe Gln Gln Leu Leu
                85                  90                  95

Gln Glu Leu Asn Gln Pro Arg Asp Gly Phe Gln Leu Ser Leu Gly Asn
            100                 105                 110

```
Ala Leu Phe Thr Asp Leu Val Val Asp Leu Gln Asp Thr Phe Val Ser
        115                 120                 125
Ala Met Lys Thr Leu Tyr Leu Ala Asp Thr Phe Pro Thr Asn Phe Arg
        130                 135                 140
Asp Ser Ala Gly Ala Met Lys Gln Ile Asn Asp Tyr Val Ala Lys Gln
145                     150                 155                 160
Thr Lys Gly Lys Ile Val Asp Leu Leu Lys Asn Leu Asp Ser Asn Ala
                165                 170                 175
Val Val Ile Met Val Asn Tyr Ile Phe Phe Lys Ala Lys Trp Glu Thr
                180                 185                 190
Ser Phe Asn His Lys Gly Thr Gln Glu Gln Asp Phe Tyr Val Thr Ser
        195                 200                 205
Glu Thr Val Val Arg Val Pro Met Met Ser Arg Glu Asp Gln Tyr His
        210                 215                 220
Tyr Leu Leu Asp Arg Asn Leu Ser Cys Arg Val Val Gly Val Pro Tyr
225                     230                 235                 240
Gln Gly Asn Ala Thr Ala Leu Phe Ile Leu Pro Ser Glu Gly Lys Met
                245                 250                 255
Gln Gln Val Glu Asn Gly Leu Ser Glu Lys Thr Leu Arg Lys Trp Leu
                260                 265                 270
Lys Met Phe Lys Lys Arg Gln Leu Glu Leu Tyr Leu Pro Lys Phe Ser
        275                 280                 285
Ile Glu Gly Ser Tyr Gln Leu Glu Lys Val Leu Pro Ser Leu Gly Ile
        290                 295                 300
Ser Asn Val Phe Thr Ser His Ala Asp Leu Ser Gly Ile Ser Asn His
305                     310                 315                 320
Ser Asn Ile Gln Val Ser Glu Met Val His Lys Ala Val Val Glu Val
                325                 330                 335
Asp Glu Ser Gly Thr Arg Ala Ala Ala Thr Gly Thr Ile Phe Thr
                340                 345                 350
Phe Arg
```